United States Patent
Griffiths et al.

(10) Patent No.: US 6,770,182 B1
(45) Date of Patent: Aug. 3, 2004

(54) METHOD FOR PRODUCING A THIN SAMPLE BAND IN A MICROCHANNEL DEVICE

(75) Inventors: Stewart K. Griffiths, Livermore, CA (US); Robert H. Nilson, Cardiff, CA (US)

(73) Assignee: Sandia National Laboratories, Livermore, CA (US)

( * ) Notice: Subject to any disclaimer, the term of this patent is extended or adjusted under 35 U.S.C. 154(b) by 650 days.

(21) Appl. No.: 09/714,410

(22) Filed: Nov. 14, 2000

(51) Int. Cl.[7] .................. G01N 27/26; B01D 57/02

(52) U.S. Cl. .............. 204/453; 204/450; 204/451; 204/454

(58) Field of Search .................. 204/450, 451, 204/453, 454

(56) References Cited

U.S. PATENT DOCUMENTS

| | | | | | |
|---|---|---|---|---|---|
| 5,429,728 | A | * | 7/1995 | Gordon | 204/453 |
| 5,750,015 | A | * | 5/1998 | Soane et al. | 204/454 |
| 5,858,195 | A | * | 1/1999 | Ramsey | 204/601 |
| 6,080,295 | A | * | 6/2000 | Parce et al. | 204/451 |
| 6,375,817 | B1 | * | 4/2002 | Taylor et al. | 204/453 |
| 2002/0008028 | A1 | * | 1/2002 | Jacobson et al. | 204/451 |

FOREIGN PATENT DOCUMENTS

| | | | | | |
|---|---|---|---|---|---|
| JP | 05072178 | A | * | 3/1993 | G01N/27/447 |

OTHER PUBLICATIONS

Ermakov et al., "Computer Simulations of Electrokinetic Injection Techniques in Microfluidic Devices," Anal. Chem. 72, pp. 351 3517 (Jun. 2000).*

* cited by examiner

Primary Examiner—Nam Nguyen
Assistant Examiner—Brian L Mutschler
(74) Attorney, Agent, or Firm—Timothy P. Evans

(57) ABSTRACT

The present invention improves the performance of microchannel systems for chemical and biological synthesis and analysis by providing a method and apparatus for producing a thin band of a species sample. Thin sample bands improve the resolution of microchannel separation processes, as well as many other processes requiring precise control of sample size and volume. The new method comprises a series of steps in which a species sample is manipulated by controlled transport through a junction formed at the intersection of four or more channels. A sample is first inserted into the end of one of these channels in the vicinity of the junction. Next, this sample is thinned by transport across the junction one or more times. During these thinning steps, flow enters the junction through one of the channels and exists through those remaining, providing a divergent flow field that progressively stretches and thins the band with each traverse of the junction. The thickness of the resulting sample band may be smaller than the channel width. Moreover, the thickness of the band may be varied and controlled by altering the method alone, without modification to the channel or junction geometries. The invention is applicable to both electroosmotic and electrophoretic transport, to combined electrokinetic transport, and to some special cases in which bulk fluid transport is driven by pressure gradients. It is further applicable to channels that are open, filled with a gel or filled with a porous or granular material.

22 Claims, 20 Drawing Sheets

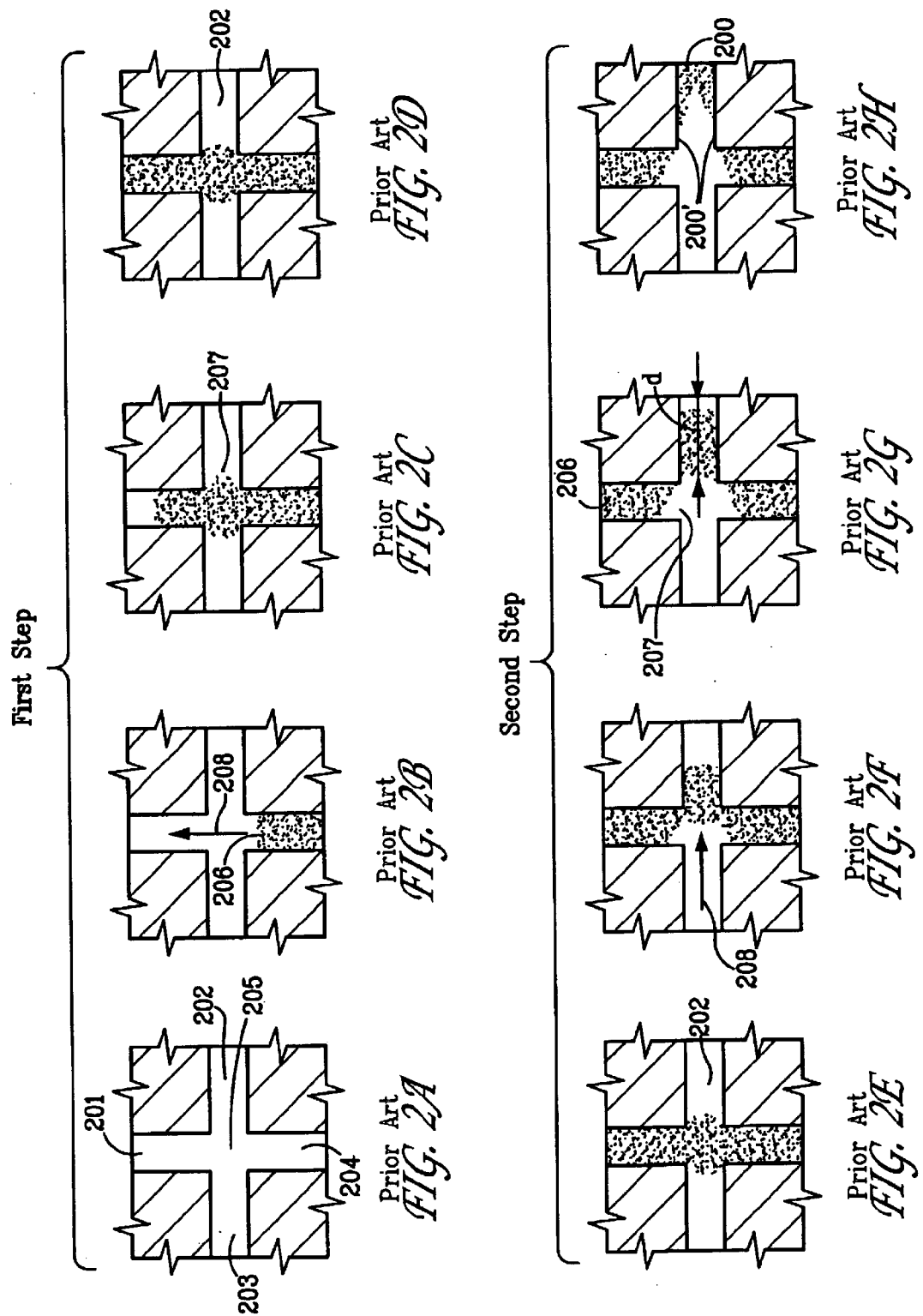

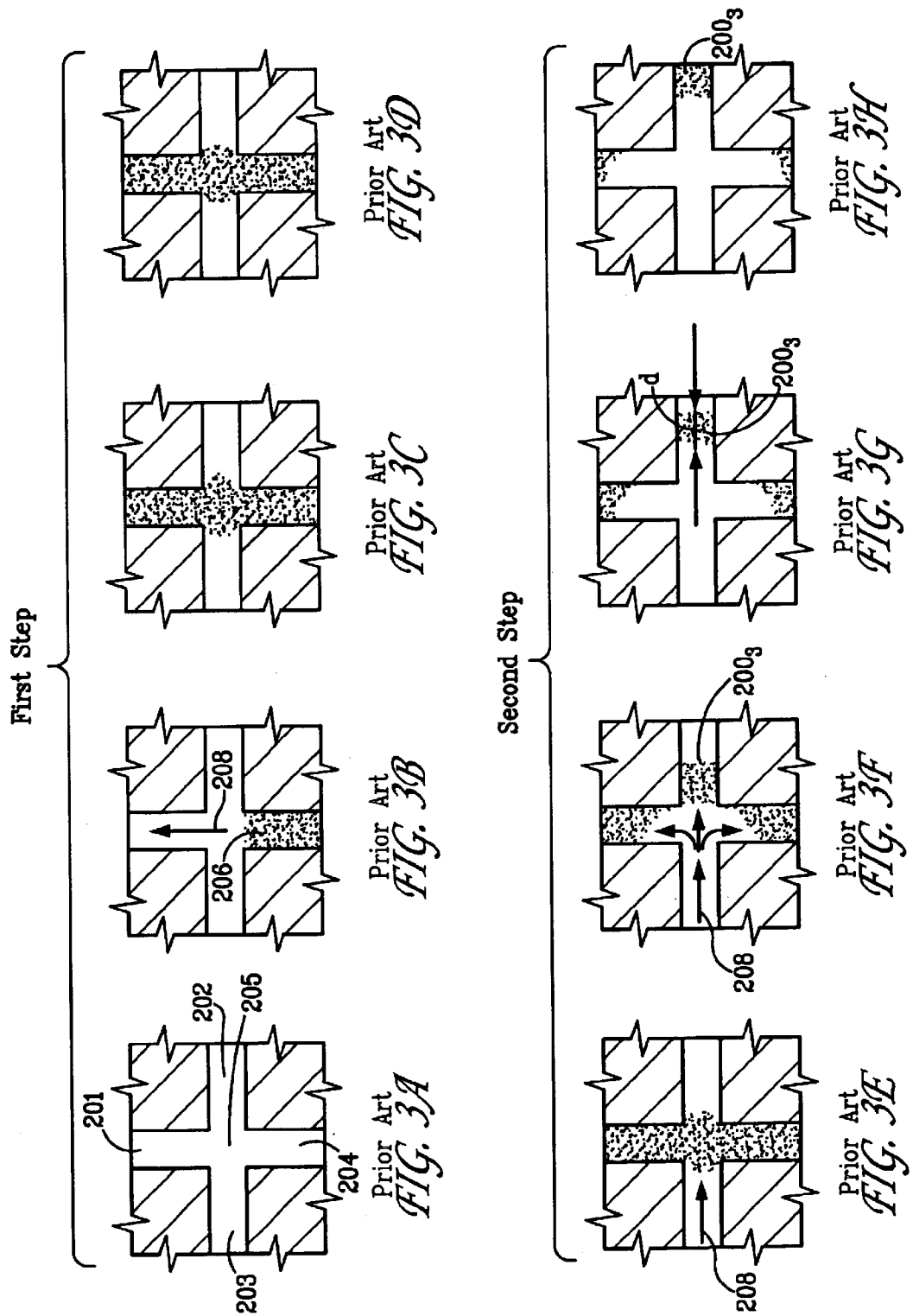

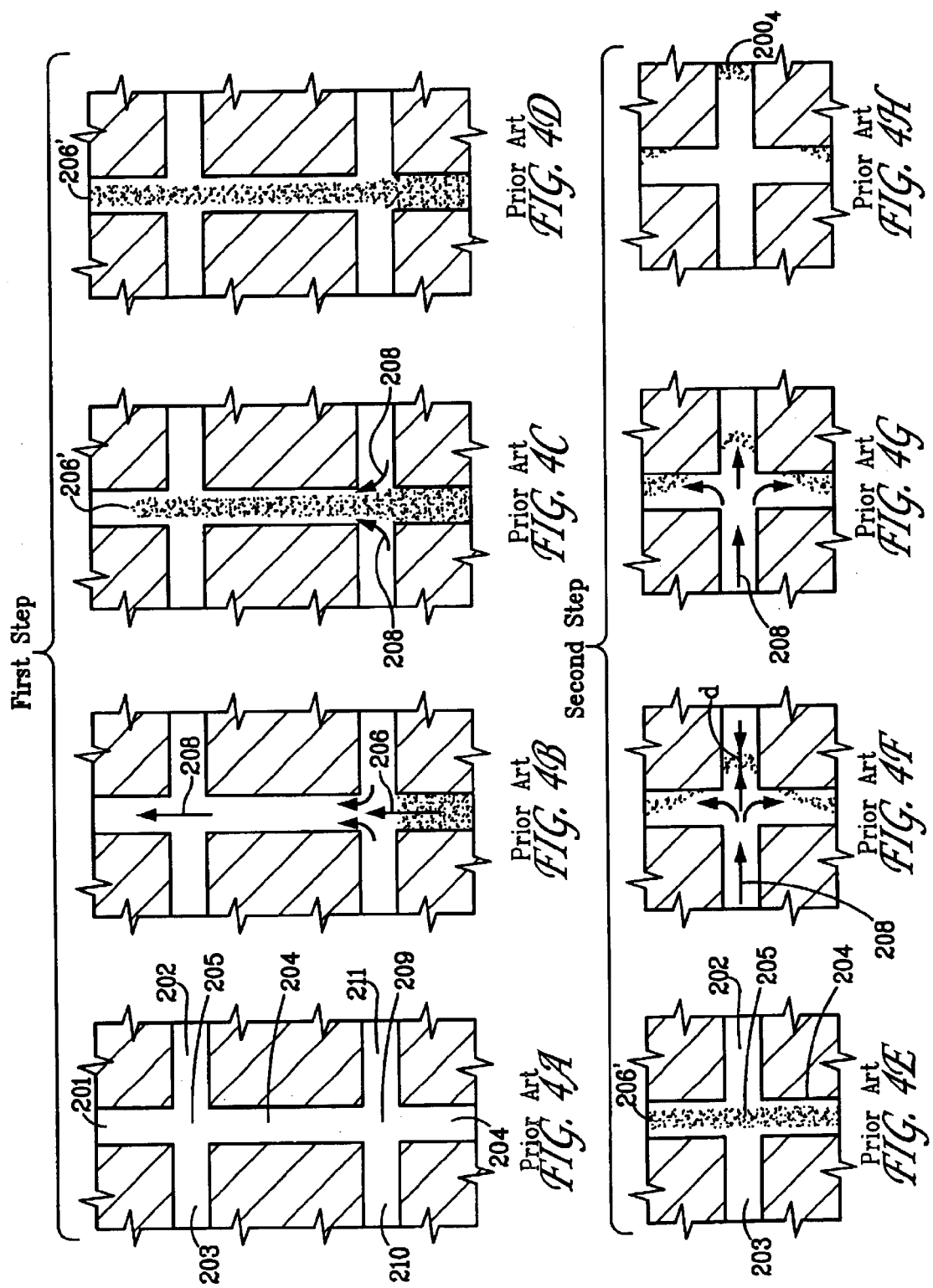

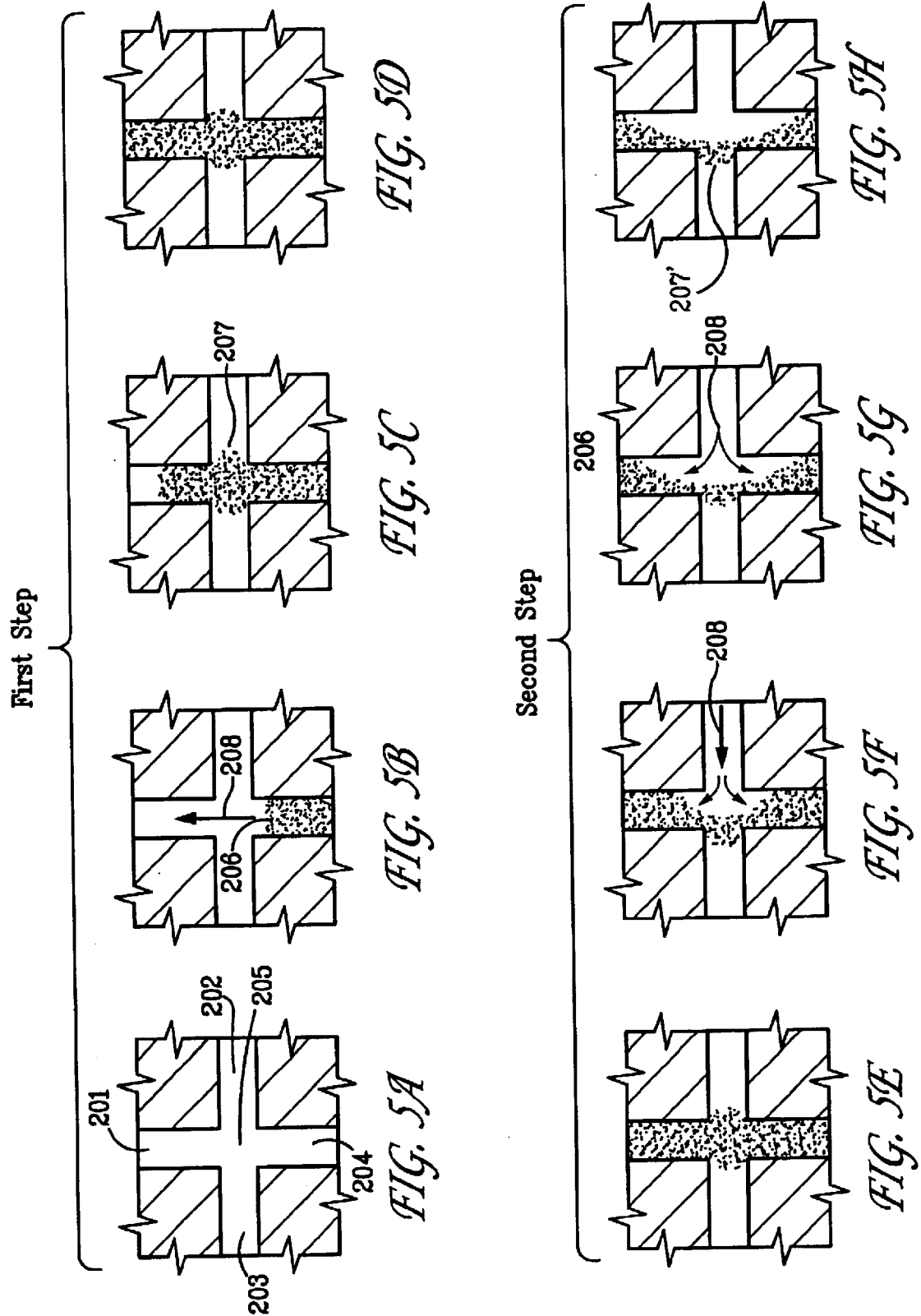

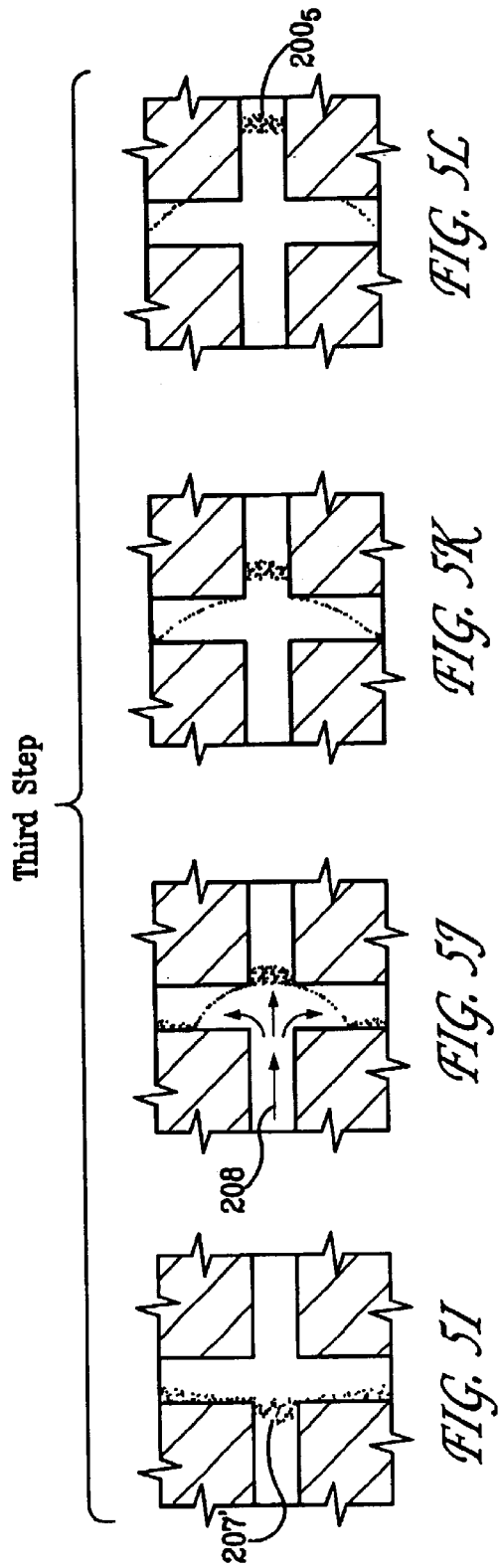
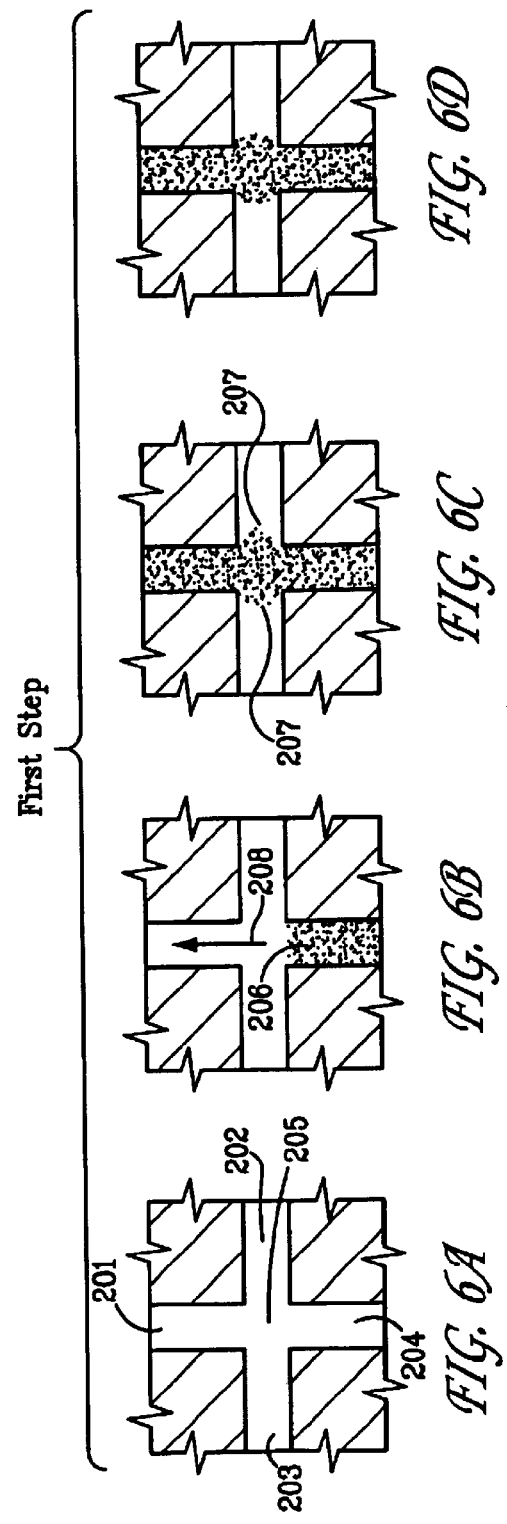

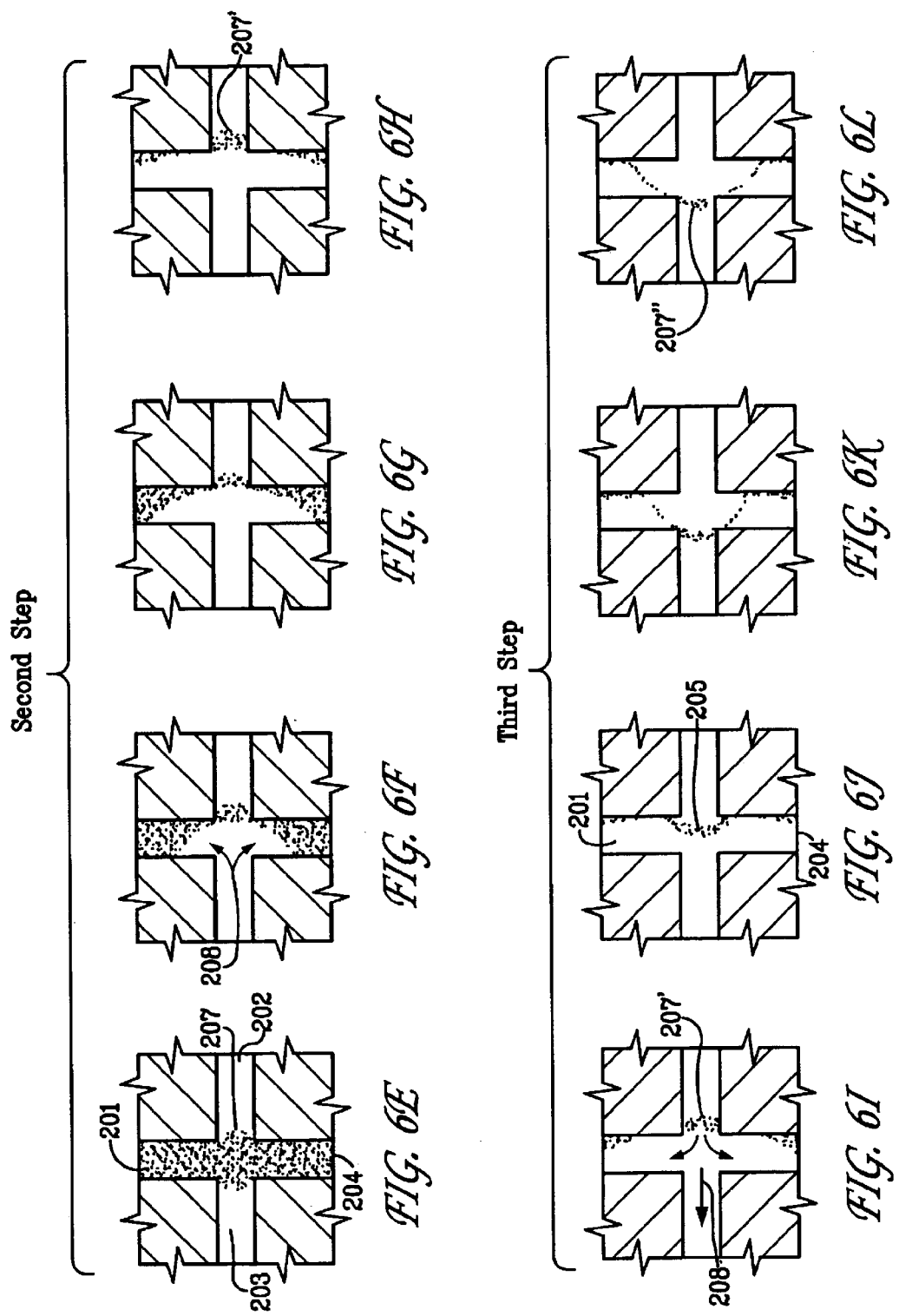

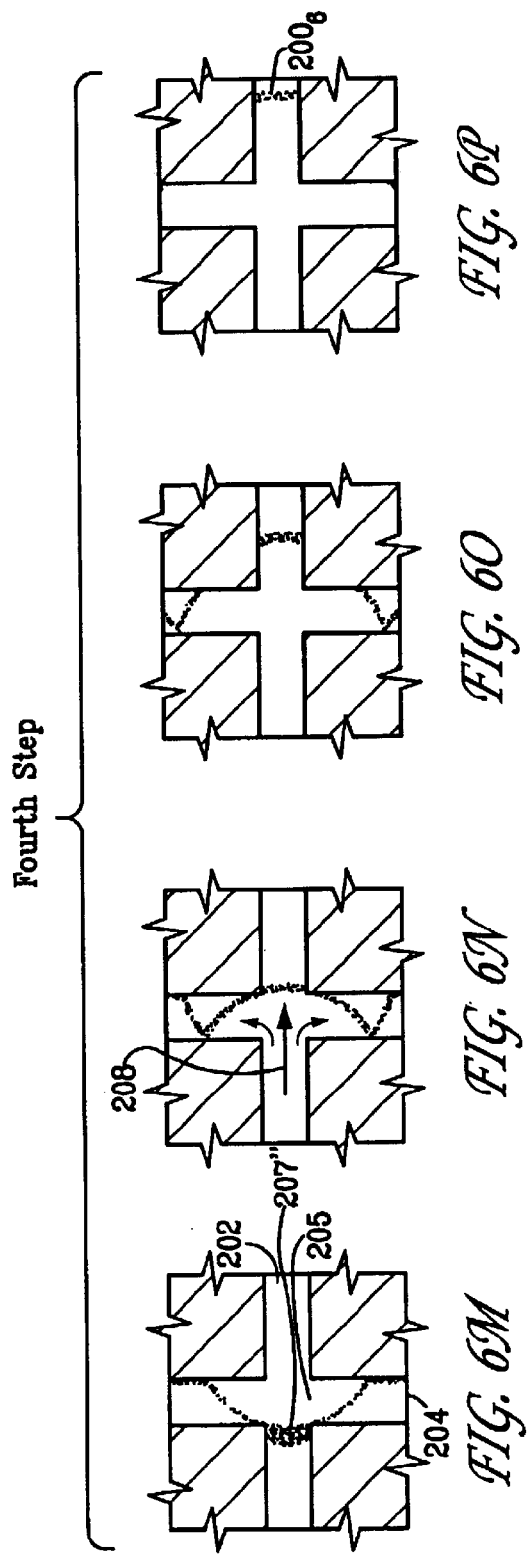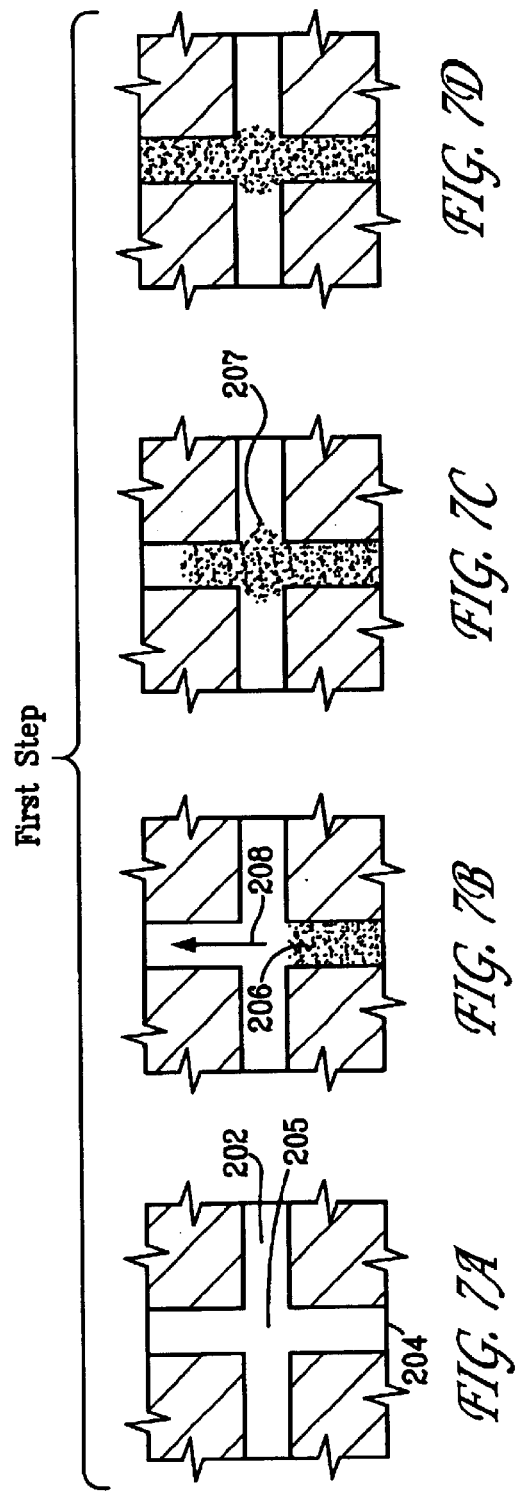

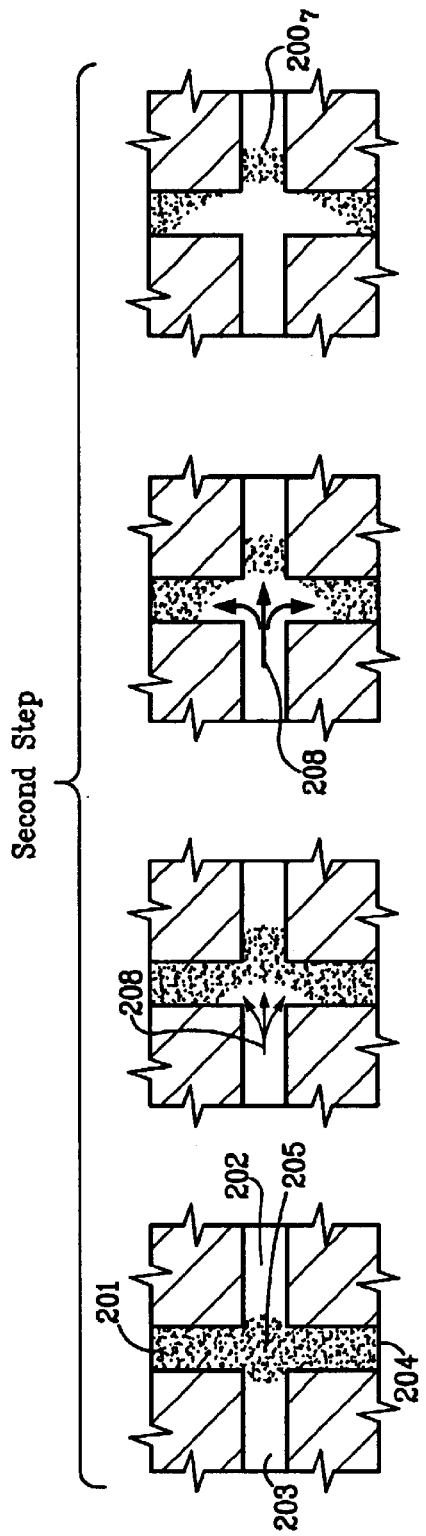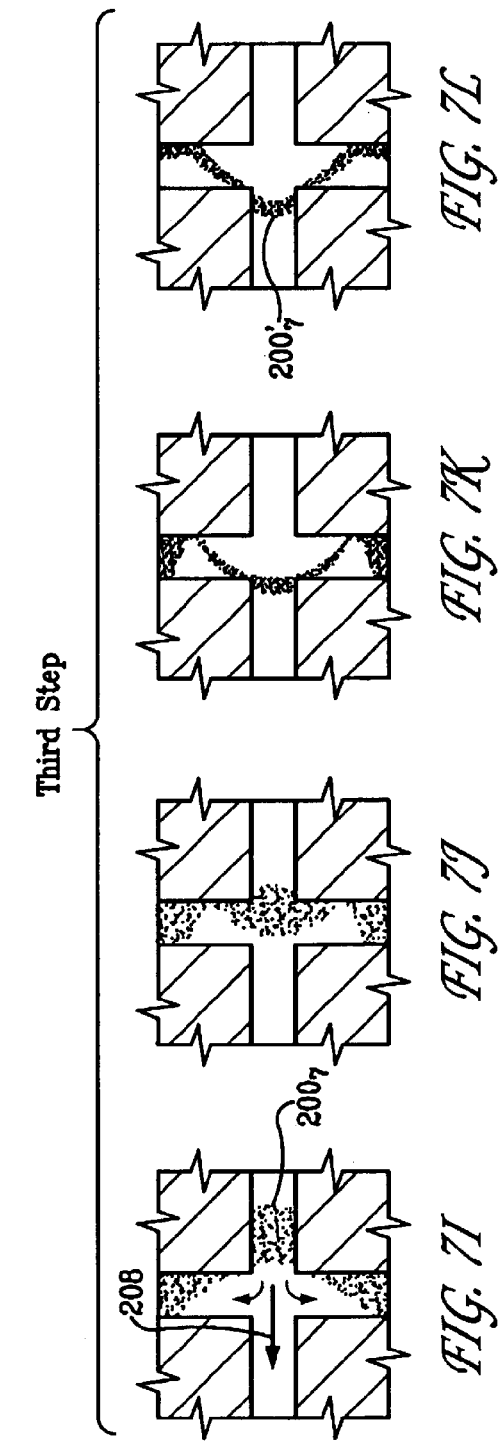

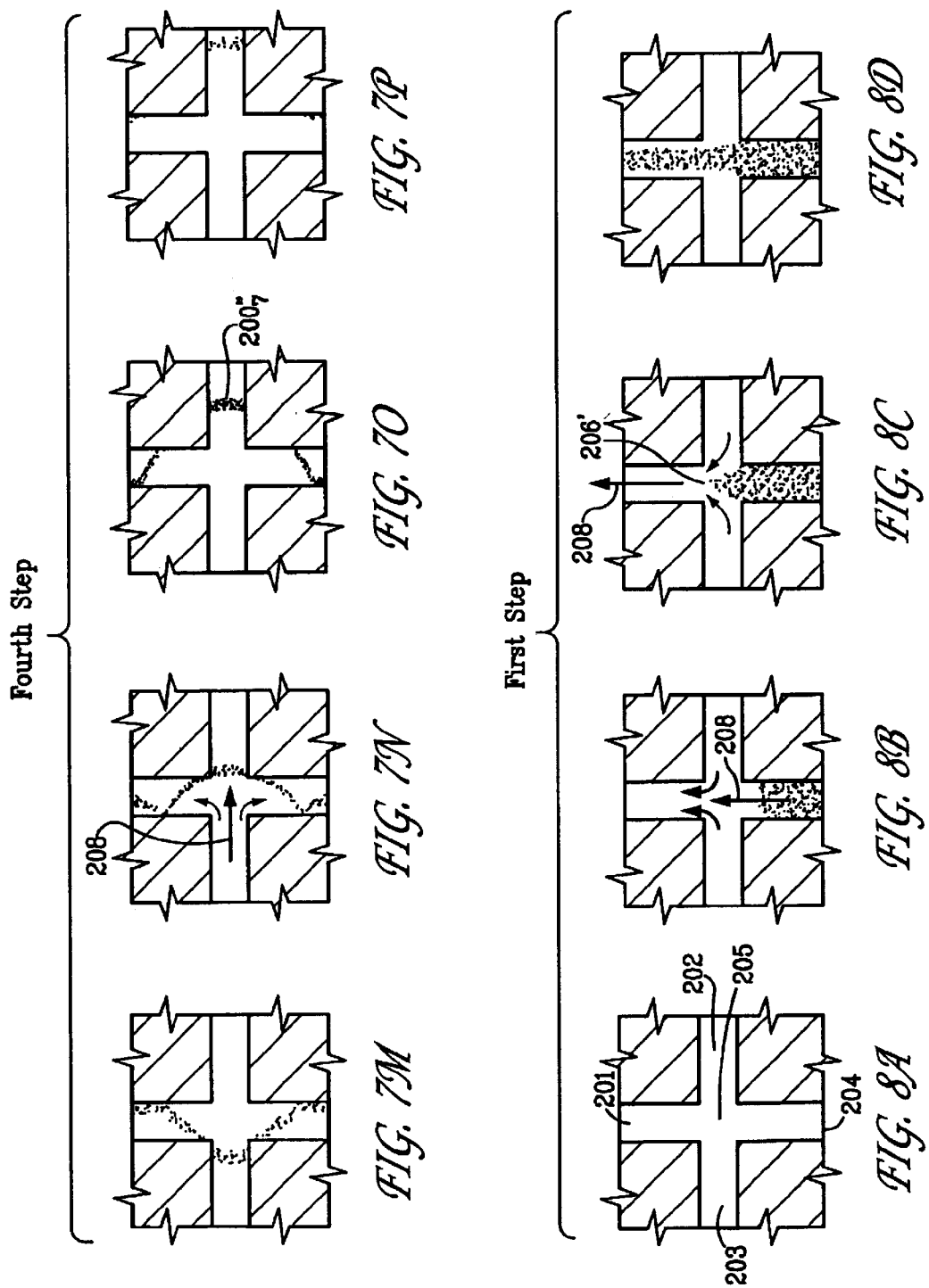

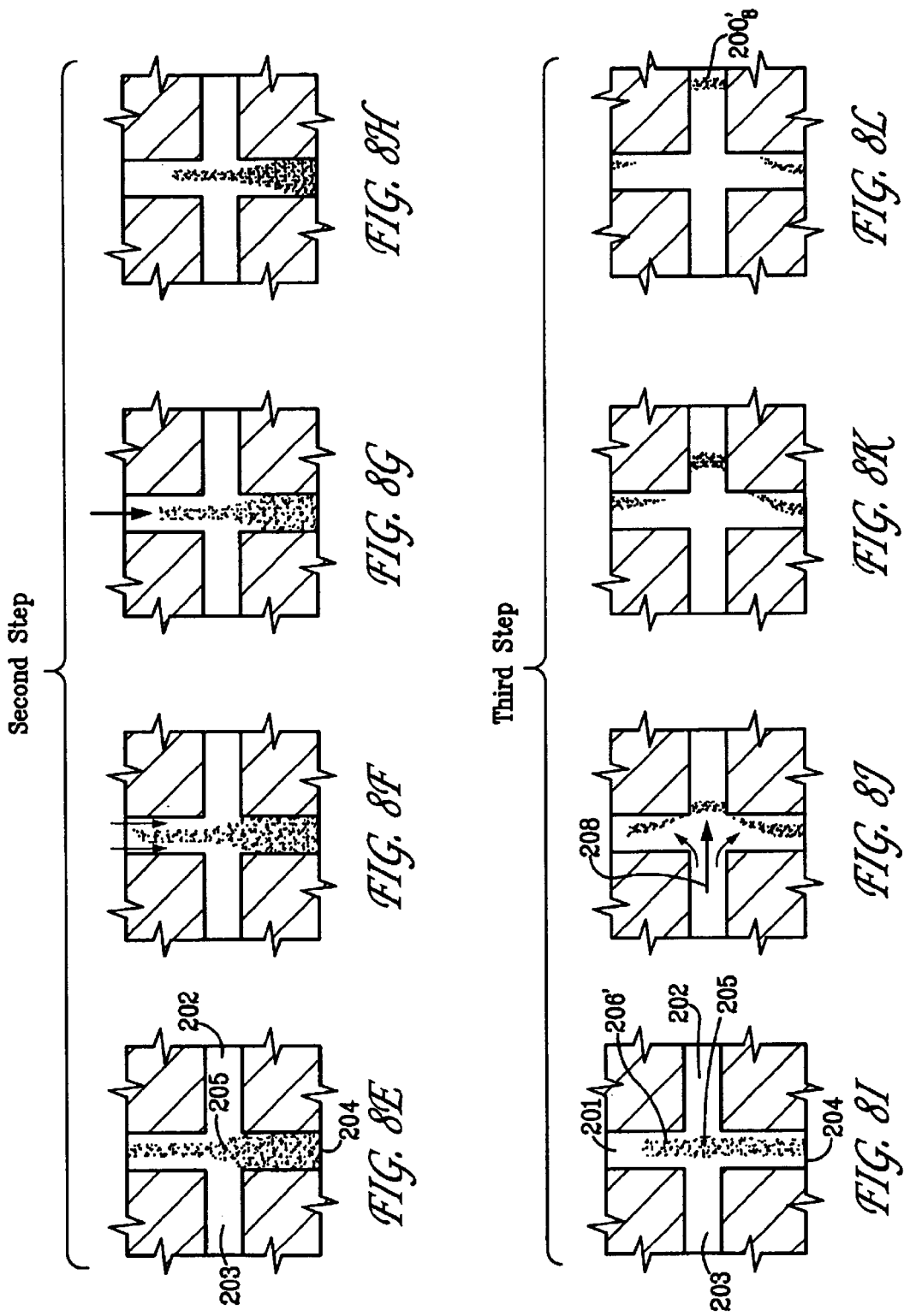

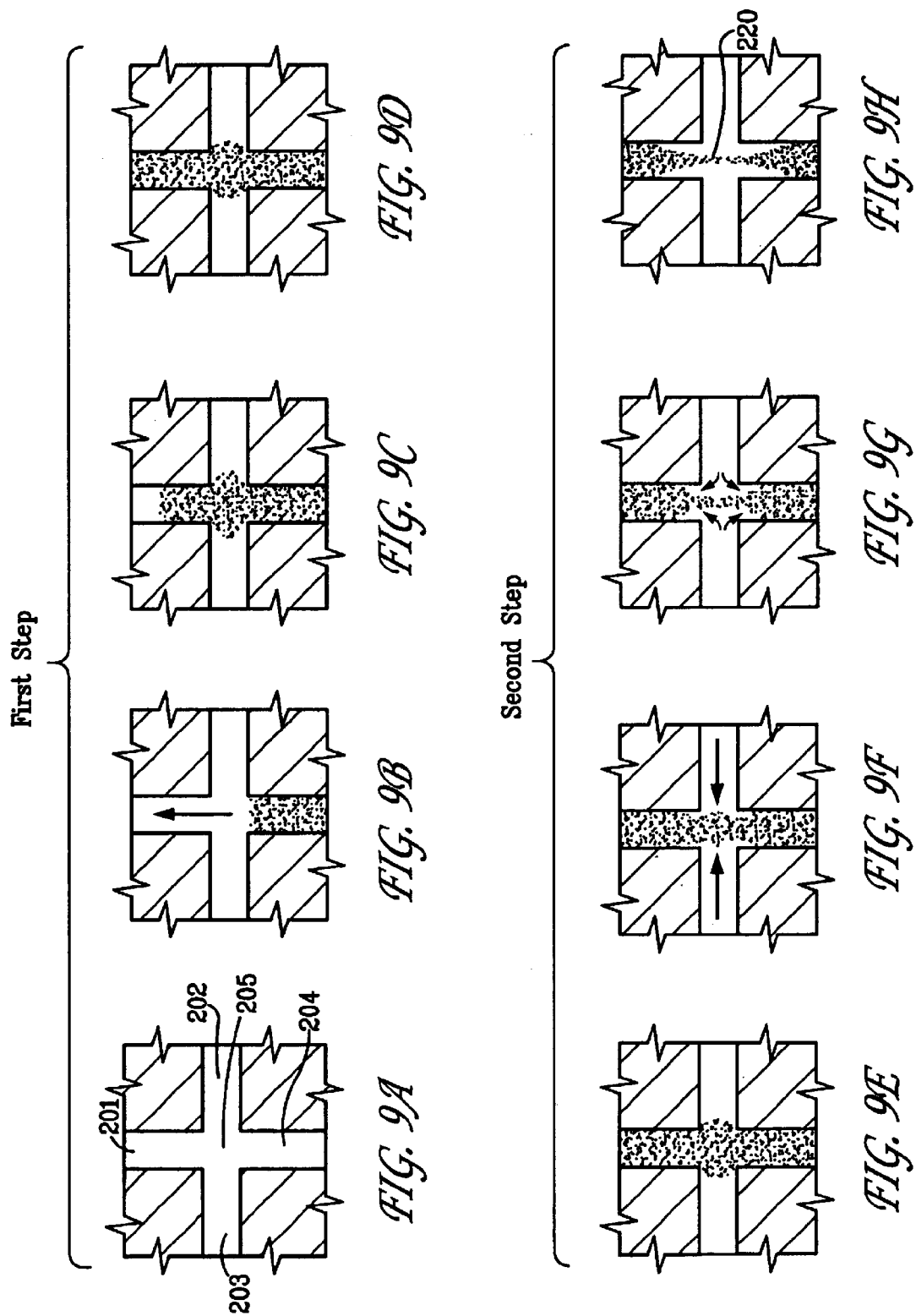

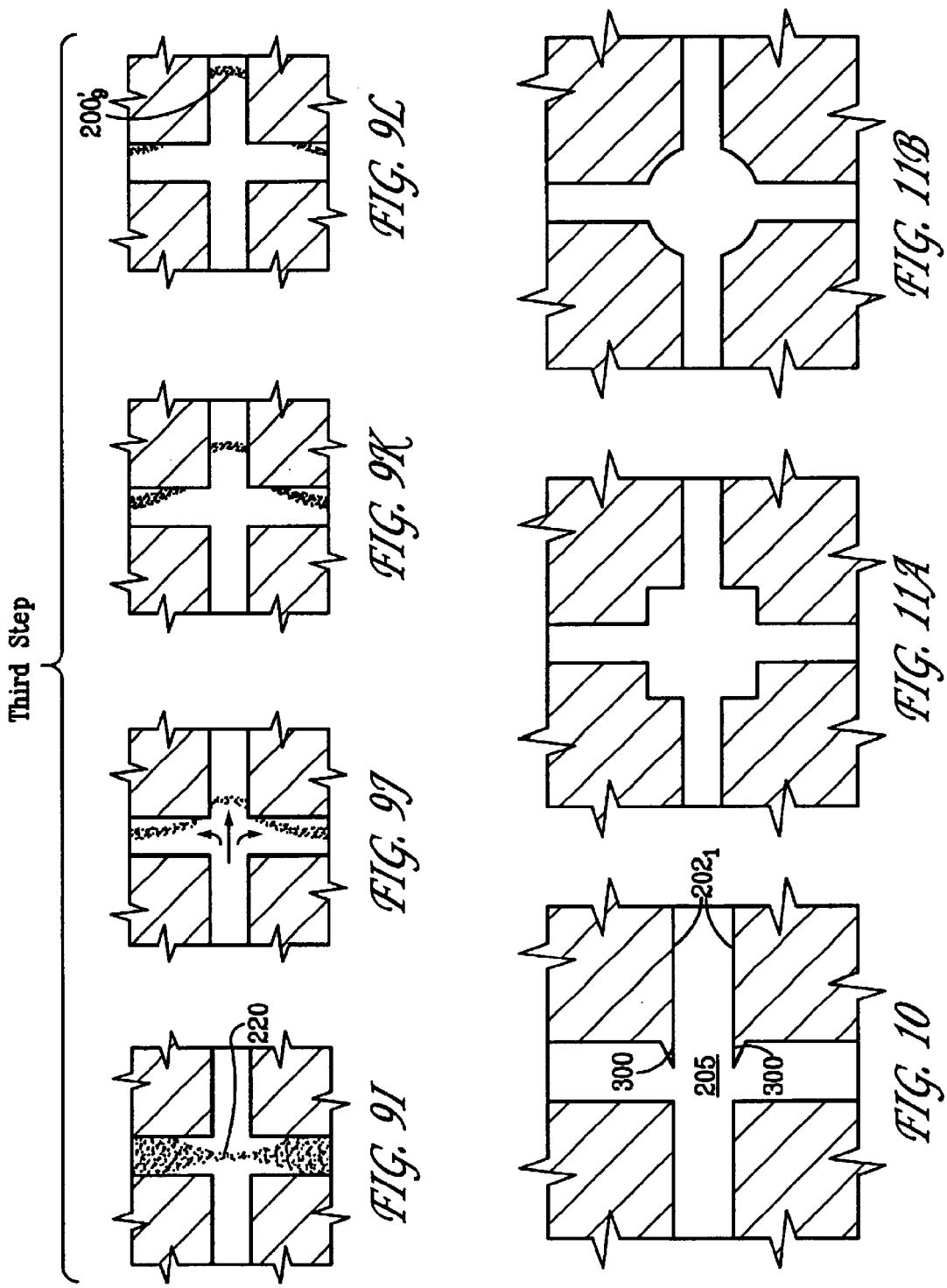

METHOD FOR PRODUCING A THIN SAMPLE BAND IN A MICROCHANNEL DEVICE

STATEMENT OF GOVERNMENT INTEREST

This invention was made with Government support under contract DE-AC04-94AL85000 awarded by the U.S. Department of Energy to Sandia Corporation, a Lockheed Martin Company. The Government has certain rights in this invention.

BACKGROUND OF THE INVENTION

Microchannel devices are finding increased use in the identification and synthesis of chemical and biological species. Employing transverse channel dimensions from a few microns to about one millimeter, such systems may permit the miniaturization and large-scale integration of many chemical processes in a manner analogous to that already achieved in microelectronics. Applications for microchannel devices now under development include such diverse processes as DNA sequencing, immunoassay, the identification of explosives, identification of chemical and biological warfare agents, and the synthesis of chemicals and drugs.

Most microchannel systems for chemical and biological analysis employ some variant of electrochromatographic or electrophoretic separation. In chromatographic processes, bulk electroosmotic motion of a fluid is induced by applying an electric field along the length of the separation column. Individual species move through the column at various speeds due to preferential adsorption on stationary surfaces such as the channel walls or an internal porous packing. In contrast, electrophoretic processes involve little or no bulk fluid motion. Here the applied electric field instead produces motion of ionic species through a stationary or nearly stationary transport medium that may be either a fluid or a gel. Species separation in electrophoretic processes occurs as a result of differing ratios of the ion charge to the ion mobility and consequent differing ion speeds.

Electroosmotic flows offer two important benefits over pressure-driven flows for transport processes in microchannel devices. First, transport speeds in electroosmotic flow are independent of the width and depth of a channel cross-section over a wide range of conditions, making this technique for driving fluid motion extensible to extremely small physical scales. In contrast, pressure-driven flows require a pressure gradient that increases inversely with the square of the minimum transverse dimension to maintain a given fluid speed. Second, the profile of the fluid velocity across the cross-section of a long straight channel is essentially flat in electroosmotic flows, again over a wide range of conditions. All transverse variation in the axial speed is confined to a small region adjacent to the channel walls and comparable in thickness to the electric Debye layer. The benefit of this flat velocity profile is that samples may be transported over long ranges with very little hydrodynamic dispersion due to nonuniform fluid speeds.

Electrophoretic processes offer somewhat different benefits in microchannel devices. Because the overall dimensions of microchannel devices tend to be only a few centimeters, very large electric fields may be produced by relatively small electric potentials. This permits larger ion speeds and reduces the overall time for separation processes. Electrophoretic motion is also easy to produce in microchannel systems since, like electroosmotic flow, only electrodes and a power supply are required to produce the phenomenon. Mechanical pumps are unnecessary. Also like electroosmotic flows, this method of producing species motion introduces little extraneous spreading of a sample band as it moves along the separation column since the electric field in a long straight channel is spatially uniform.

Despite these benefits in long-range transport, electrokinetic mechanisms are not particularly well suited to producing a thin sample band for subsequent processing in a separation or other process channel. The reason for this is that species motion in both electroosmotic and electrophoretic transport processes is governed by the highly-diffusive Laplace equation, and the region over which motion is induced usually occupies at least one channel width. As a result, the thickness of a sample band produced by such motion will usually exceed the channel width; this is not acceptable for many processes of practical interest.

For electrochromatographic and electrophoretic separation processes, the thickness of the initial sample band measured in the direction of the sample motion may need to be small compared to the channel width. Separation columns in microchannel systems are typically not very long, so final spacings between constituent bands may span only a channel width or so. To resolve these bands requires that the thickness of the sample band initially injected into the column is much smaller than the band spacing or, equivalently, much smaller than the channel width. In addition to separation processes, small sample sizes and sharp definition of species interfaces are also desirable during routine sample transport. These desired characteristics allow more precise control over processes such as mixing, dilution and synthesis.

The invention described here provides a method and apparatus for producing a sample band for subsequent processing wherein the thickness of the band in the direction of sample motion is small compared to the channel width. Further, the thickness of the band may be controlled to provide a desired sample volume or size. This method can even produce sample bands having an overall thickness an order of magnitude or so smaller than the channel width. The method can be implemented using conventional channel geometries and conventional electrical hardware. Additional benefits can be obtained by using these new methods in conjunction with improved channel geometries. Such improved geometries are also disclosed here.

Prior Art

FIG. 1 schematically illustrates a very simple microchannel system 100 for chemical analysis. Here, the channels are fabricated on a planar substrate 101. Reservoirs 102–105 have access ports (not shown) that permit introducing and extracting fluid through the top or bottom faces of the substrate. Channels 112–115 are filled with a fluid or gel-material hereinafter referred to as a "transport medium," which supports migration of ions or charged particles of a sample material either through or with the transport medium under the influence of an applied electrical field. The process channels 112–115 may also contain a separation matrix comprising a porous or granular material, a microfabricated pattern of obstacles, or a plurality of protrusions that promote species separation. The reservoir access ports (not shown) may also be used to control the hydrostatic pressures in the reservoirs or they may be left open to maintain reservoir pressures equal to the atmospheric pressure. Similar access holes (not shown) are used to insert electrodes 106–109 that are connected to power supply 110 through leads 106'–109' respectively.

Power supply 110 is used to apply electric fields along one or more of channels 112–115 emanating from junction 111.

The electric field is the negative of the gradient of the electric potential. The overall electric field is applied by controlling the differences in electric potential between the reservoir electrodes or, equivalently, by controlling the electric current flow to the individual electrodes. Although the electric field within the junction region is generally multidimensional, the electric field and induced sample transport is nearly one dimensional and uniform along straight channel segments, provided that the Debye layer thickness is small compared to the transverse channel dimensions. Under this restriction, easily met by most practical systems, the electrokinetic transport speed is simply proportional to the electric field at any point within the channels or junction. Thus, control of the electric field is equivalent to controlling the sample transport speed.

In a separation process, different species within a sample band (not shown) move along process channel 112 (or separation column) at different speeds due to differences in surface adsorption or differences in ion charge and mobility. As a result, the sample separates into a series of constituent bands that are detected as they pass through a detection device 120, located toward the end of process channel 112. The contents of the sample are inferred from the observed arrival times of the separated bands. Since the measurement resolution depends on physical separation between the bands, it is desirable that the bands be as distinct and sharply defined as possible.

The spacing between constituent bands is generally proportional to the length of the separation column. Because microchannel devices are intended to be small, separation columns in these devices tend to be short by conventional standards and rarely exceed several centimeters. As a result, the spacing between constituent bands at the detector location may be only a fraction of the channel width. Because band spacings less than the initial thickness of the sample cannot be resolved as distinct entities, the initial thickness of the band injected into the process channel must also be small compared to the channel width. More generally, the thickness of the injected band must be as small as possible to provide maximum resolution for all band spacings, while at the same time providing just sufficient sample volume for accurate down-stream detection.

To produce a sample band and inject it into process channel 112 of system 100, the sample material is first introduced into the lower supply channel reservoir 103 and then transported through supply channel 113 by applying an electric field along supply channel 113 and waste channel 114. This field is applied by using the power supply to impose a potential difference between the electrode 107 in the supply reservoir 103 and the electrode 106 in the waste reservoir 102 terminating waste channel 114. During this step of the process, the power supply prevents any current flow to electrodes 109 and 108 located in the buffer and process reservoirs 104 and 105, respectively, so as to prevent any significant transport along the buffer and process channels, 115 and 112. After completing this step, the junction 111 is filled with sample material (not shown). This volume of sample material contained within the junction is then transported into the process channel 112 to form the sample band. The sample transport during this step is induced by applying an electric field along buffer and process channels 115 and process channel 112 using the buffer and process channel electrodes 109 and 108 respectively. During this step the power supply prevents current flow along the supply and waste channels. However, because the electric field lines tend to bulge from the primary channel into the ends of the supply and waste channels, sample material is removed from the supply and waste channels, forming a tail on the sample band as it is transported along the process channel. As a result, a sample band produced in this manner generally has a thickness that exceeds the channel width.

In order to illustrate the process and to promote an understanding of the invention a series of illustrations follows. The schematic diagrams of sample motion, shown in FIGS. 2–9, are based on a series of detailed computational simulation using a variety of conditions and parameters beginning with the prior art configuration. The computational model used to perform the numerical simulations is described below in the section entitled "Detailed Description of the Invention." The actual graphical output of each of the computer simulations represented by FIGS. 2–9, is shown in the corresponding FIGS. 12–19. As will be explained below, the model and the computed results are equally applicable to sample transport by electroosmotic or electrophoretic means or to any combination of these two transport mechanisms.

FIG. 2 schematically illustrates the sample transport for the conventional two-step process (described above) used to produce a sample band 200 and inject it into a process channel 202. The first step of this process is shown in the upper sequence of frames comprising FIGS. 2A–2D. These frames illustrate the behavior of flow through channels 201–204 at four succeeding instants in time. Time increases from left to right, with each frame later than the preceding frame by a discrete increment of time, $t_i$. The lower sequence of four frames (FIGS. 2E–2H) illustrates the second step of the process, again read from left to right. The first frame, FIG. 2E, of the second step (second row) is identical to the last frame, FIG. 2D, of the first step (first row). For the sake of clarity and to promote a better understanding of the invention, only the channel segments near the junction 205 are shown. Furthermore, those regions within the channel which are occupied by sample material are illustrated as comprising a plurality of black dots, analogous to tracer particles that are carried along with the sample, again for clarity.

In the first step, (FIGS. 2A–2D) sample material 206, represented by black tracer particles, is transported from supply channel 204 through junction 206 and along the waste channel 201 by applying an electric potential between the supply and waste reservoirs (not shown). These potentials establish an electric field that drives sample transport along the supply channel, through the junction, and into and waste channel. The direction of fluid motion, or species migration, is indicated by arrows 208. Unintended lobes 207 of sample material 206 also penetrate about one channel width into process channel 202 and buffer channel 203. This penetration results from bulges in the electric field lines extending into the process and buffer channels, 202 and 203 respectively, not from diffusion. Once the junction 205 is completely filled, as in FIGS. 2C and 2D, the first step of this conventional process is terminated by removing the applied electric field.

As noted above, the second step in the conventional two-step process is illustrated in the sequence of frames FIGS. 2E through 2H. Here, an electric potential is applied between the reservoir electrodes (not shown) terminating buffer channel 203 and process channel 202 to produce sample motion to the right, indicated by arrow 208 in FIG. 2F, injecting a sample band into the head of process channel 202. However, as seen in the last two frames (FIGS. 2G and 2H), the thickness, d, of sample band 200, is more than twice the channel width. In addition sample band 200 is even further elongated by long trailing tails 200'. These tails result from bulges in the electric field lines now extending into the waste and supply channels, 201 and 204. Since the electric field is relatively weak in side lobes 207, sample material 206 is released very slowly from the vertical supply and waste channels into the process channel 202. The end result is an injected sample band 200 having an effective thickness of three to four channel widths.

To reduce the thickness of injected samples and to help eliminate sample tails, improved methods of sample manipulation have been explored in the prior art. FIGS. 3A–3H illustrate an improved prior-art two-step method used in the prior art to produce and inject a sample band. This improved method reduces the thickness, d, of the sample band 200 and largely eliminates the long trailing tails 200' shown earlier in FIGS. 2A–2H. The first step in this method is the same as shown previously; the top set of frames, FIGS. 3A–3D, are identical to those in FIGS. 2A–2D. The sample material 206 is first transported along the supply channel 204, through the junction 205 and then toward the waste channel reservoir (not shown). The lower frames, FIGS. 3E–3H, show subsequent transport of the sample band 200 into the process channel 202. In contrast to FIGS. 2A–2H, the electric potentials of FIGS. 3A–3H are applied to the four reservoir electrodes (not shown) in a manner that causes transport (shown as arrows 208 in FIG. 3F) from the buffer channel 203 into the supply 204, waste 201, and process 202 channels, injecting sample band 200$_3$ into the process channel 202. In the last two frames, FIGS. 3G–3H, the sample band is moving from left to right along the process channel toward a detector (not shown), while other portions of sample material are moving from the junction 205 toward both the supply and waste reservoirs (not shown).

In the second step of the process, FIGS. 3E–3H, the field is applied by setting the electrode potential of the buffer reservoir above the potential of each of the other three reservoirs. In general, however, the required polarity of the applied field depends upon the sign of the Zeta potential in electroosmotic flows while in electrophoresis the required polarity depends on the sign of the charge on the ion species comprising the sample. In the particular example shown in FIGS. 3E–3H, the magnitude of the applied electric field in the waste, process and supply channels, 201, 202, 204 respectively, is the same. However, this need not be the case, in general, provided that the mean transport speeds in supply and waste channels 204 and 201 are a significant fraction of the mean transport speed in process channel 202.

The improved method shown in FIGS. 3A–3H is capable of reducing the thickness, d, of the resulting sample band 200$_3$ by about a factor of two. This limitation is based on the simple observation that about half of the sample volume in junction 205 at the beginning of the second step (FIG. 3E) is ahead of the center of the junction. Thus, even if transport speeds in the supply and waste channels 204 and 201 are increased dramatically during this step, it is not possible to reduce the effective sample thickness, d, to less than about one channel width. However, this approach does effectively eliminated the long tails 200' that would otherwise follow sample band 200$_3$ into process channel 202.

Recognizing the need for further reduction in the thickness of sample bands, Jacobson and Ramsey (Anal. Chem. 1997, 69, 3212–3217) proposed a sample focusing technique which they have demonstrated in computational and experimental studies. Their basic concept, as it relates to preparation of sample bands is illustrated in FIGS. 4A–4H. For convenience, the discussion immediately below uses language appropriate to electroosmotic flow, though the same procedure is also applicable to sample transport by electrophoresis.

The first step of the process, shown in FIGS. 4A–4D, illustrates the geometry of the focusing apparatus and the first step in this method. The apparatus consists of two connected junctions 205 and 209; the upper junction 205 plays the same role as those in previous figures while the lower junction 209 is for focusing the sample material 206.

During the first step, shown in FIGS. 4B and 4C, sample material 206 enters the lower focusing junction 209 from below, through the supply channel 204, while a buffer fluid enters junction 205 from both the left and the right in opposite (countervailing) directions, through focusing channels 210 and 211. Flow directions in the vicinity of junction 209 are shown as arrows 208. The incoming buffer streams from the focusing channels 210 and 211 enter focusing junction 209 to restrict and confine the width of the sample stream 206 as it moves toward the upper junction 205 thereby forming focused sample stream 206' so that it occupies only a fraction of the width of supply channel 204, in this case about one-third of that width. As before, focused sample stream 206' has bulged slightly toward both process and buffer channels 202 and 203, producing reduced lobes 207'. Here, the extent of bulging is greatly reduced because the focused sample stream 206' crosses the upper junction 205 very near to the centerline of the supply and waste channels 204 and 201. The width and the position of a focused sample stream 206' are generally controlled by the relative fluid speeds in left, right and lower channel legs 210 and 211 of the focusing junction 209. Focusing thus offers a means of controlling the thickness, d, of a sample band 200$_4$ without altering the channel geometry.

FIGS. 4E–4H illustrate step 2 of this improved method, whereby a portion of the focused sample stream 206' is injected into process channel 202 to produce the final sample band 200$_4$. Note, that the lower focusing junction 209 is omitted from these lower frames. At the beginning of this step, the focused sample 206' has already been transported through junction 205. The sample band is formed by raising the electric potential in the buffer channel reservoir (not shown) relative to that of reservoirs terminating the supply, waste and process channels (not shown). This step is therefore the same as the second step of the method shown earlier in FIGS. 3E–3H, with the exception that here the initial thickness of the sample stream 206 has been reduced to produce focused sample stream 206' using a focusing junction 209 as described above. We see in FIGS. 4F and 4G that the thickness, d, of the resulting sample band 200$_4$ is not substantially altered during the final step. We also see that the thickness, d, of the resulting sample band is greatly reduced relative to that produced by the methods previously illustrated in FIGS. 2 and 3.

Although the sample focusing method described above and shown in FIGS. 4A–4H can produce a thin sample band 200$_4$, and provides a means for controlling the sample band thickness, d, it does require the use of auxiliary channels 210 and 211, junction 209, additional buffer reservoirs (not shown), and added electrodes, fill ports, and electrical connections (not shown), in order to perform the focusing process.

In summary, the simplest prior-art process produces a sample band thickness of at least two to three channel widths (FIGS. 2A–2H). This can be reduced to about one channel width by inducing transport away from the junction into the supply and waste channels as the sample band is transported into the process channel (FIGS. 3A–3H). Another procedure of prior art, known as sample focusing, is effective at producing a sample band having a thickness that is small compared to the channel width (FIGS. 4A–4H). However, this approach requires an additional focusing junction and additional channels, reservoirs, electrical connections and controller channels.

The Present Invention

To overcome the shortcomings of the prior art, the present invention provides a new method for producing sample bands having a controlled thickness that may be far less than the widths of the channels. The new approach comprises two primary steps: (1) inserting an initial sample band into one leg of a junction and (2) thinning of the initial sample band by transporting it across the junction one or more times using a diverging flow field within the junction to stretch and thin the sample. The first step may be performed by one of the prior art methods already shown in FIGS. 2A–2D or 3A–3D or, alternatively, by a new method, unique to the present invention, that substantially reduces the thickness of the inserted sample band. The second step, that of thinning the sample band, is also unique to the present invention. This thinning step may comprise a number of steps or repetitions in which the sample is transported back and forth across the junction. At the end of the final thinning step, the sample band is injected into the head of the process channel, ready for subsequent processing.

An important advantage of all embodiments of the present invention is that they rely only on altering the sequence of applied electric fields to control the volume and thickness of the sample band. The required microchannel hardware comprises simply a junction formed at intersecting channels and a power supply to control the electric fields in each of the channels. The geometries of the junction and channel network are not critical and need not be altered in any way from existing or conventional designs. In particular, there is no need for channels of varying or differing depth. Of course, alterations to the channels and junction can be made to optimize these methods, and the channels abutting the junction may have the same or differing widths. However, with or without these geometric alterations, the present methods can be easily implemented using existing technology and existing hardware.

The present methods can be used to reduce the injected sample thickness by any desired degree, provided that the transport speeds used during sample manipulation are sufficiently high. The use of these high speeds reduces the extent of molecular diffusion of the sample band during manipulation. Finally, these new methods may be employed using multiple junctions distributed along a single buffer/process channel to inject multiple sample bands into one process stream. They may also be employed using multiple buffer/process channels to simultaneously inject one or more samples into each.

The present invention, therefore, provides a simple means for reducing and controlling the thickness of injected sample bands and does not require additional focusing channels, reservoirs or electrical hardware to accomplish this result.

SUMMARY OF THE INVENTION

The new method of producing a thin sample band in a microchannel system comprises a series of steps in which the sample is manipulated by controlled transport through a junction. The junction is formed at the intersection of two primary channels, the buffer and process channels, running in one direction (the primary axis) and a pair of side channels, supply and waste channels, usually running in a nominally perpendicular direction (secondary axis). The first step of the new method is insertion of a sample band into one of the primary channels. The insertion step can be performed in either of the conventional fashions shown earlier in FIGS. 2 and 3, or by using a new insertion process described just below.

The first step of the new insertion procedure is to transport sample material from a supply channel through the junction and out the waste channel. In the second step of insertion, unique to the present invention, the sample volume within the junction is reduced and positioned to produce an initial sample band. During this second step of insertion, sample material enters the junction from either the buffer or the process channel and leaves the junction along the supply and waste channels. The transport during this step is induced by applying electric fields along three of the four channels, while preventing current flow along the remaining channel containing the initial sample band at the end of the step.

After this insertion step, the thickness of the initial sample band may be reduced by one or more thinning steps, also unique to the present invention. During these thinning steps, the applied electric field induces sample transport from one of the primary channels (buffer or process) toward the other three channels. As the sample band moves across the junction, it is stretched and thinned by the diverging transport field within the junction and part of the sample band is transported into the side channels (supply and waste). In multiple thinning steps, the sample band moves back and forth across the junction, each time stopping and reversing direction before or slightly after it enters the buffer or process channels. After thinning to a desired thickness, the sample band is injected into the head of the process channel.

In addition to these new methods of sample insertion and sample thinning, the present invention also describes a new procedure for performing focusing of a sample stream and injection of a sample band within a single junction. The prior art of FIGS. 4A–4H required two junctions to perform the same task. This new method employs a three-step process comprising: a first step in which a sample stream is transported into a junction using transport from intersecting channels to focus the sample stream; a second step in which the narrow focused stream is transported in the reverse direction so that the focused portion of the sample stream extends across the full width of the junction; and a third step in which a portion of the focused stream is injected into a process channel.

In addition to these new processes, the new apparatus of the present invention provides improved junction and channel geometries that increase the thinning that occurs each time the sample band traverses the junction and reduce the bow of the final sample band. Increased thinning results from enlarging the junction beyond the bounds of the channel intersection. Bow is reduced by cusp-like extensions to the process channel walls, protruding into the junction. These extensions increase the axial sample speed along the channel walls near the channel inlet, allowing the band to enter the process channel with little bowing in the direction of motion. Similar extensions to the supply, waste and buffer channels are also beneficial for some more sophisticated methods of producing and injecting a sample band. This new apparatus may be used either with previously developed methods of sample manipulation or with the improved methods of the present invention.

The present invention, therefore, provides a method and apparatus for producing a sample band and injecting it into a process channel such that the thickness of the sample band is small in the direction of its motion but which occupies the full width and height of the channel.

Furthermore, the present invention provides a means for varying and controlling the thickness of the sample band by controlling the sequence and magnitude of electric fields applied along each channel, without modification of the channel and junction geometries.

Another object of the instant invention is to provide a new method for improving the performance of microfabricated devices used for analysis, synthesis and other processes involving chemical and biological species.

Further, by providing a means for controlling the thickness of initial sample bands, the present invention provides a means for improving the resolution of separation processes used to identify different chemical species by differences in their arrival times near the end of the process channel.

It is yet another object of this invention to provide a means for improving the resolution of separation processes or other processes in which thin, sharply defined chemical bands are desirable.

It is yet another object that this invention be applicable to both electroosmotic and electrophoretic processes driven by applied electric fields.

It is a further object of this invention that it be applied to microchannel devices comprising channels that are filled with a fluid or with a gel. In addition to these fluid and gel transport media, the transport channels may also contain a separation matrix comprising a porous or granular material or microfabricated patterns of obstacles or surface protrusions.

It is another object of this invention to provide an improved junction design comprising a cusp-like extension, or extensions, on the process channel walls, protruding into the junction, for increasing the axial transport speed of the sample band along the channel walls near the channel inlet.

BRIEF DESCRIPTION OF THE DRAWINGS

FIGS. 2A–2H illustrate a conventional method for producing and injecting a sample band. The illustration is based on the simulation results shown in FIG. 12.

FIGS. 3A–3H illustrate a conventional method for producing and injecting a sample band. The illustration is based on the simulation results shown in FIG. 13.

FIGS. 4A–4H illustrate a conventional method for producing and injecting a sample band. The illustration is based on the simulation results shown in FIG. 12.

FIGS. 5A–5L illustrate a conventional method for producing and injecting a sample band. The illustration is based on the simulation results shown in FIG. 15.

FIGS. 6A–6P illustrate a conventional method for producing and injecting a sample band. The illustration is based on the simulation results shown in FIG. 16.

FIGS. 7A–7P illustrate a conventional method for producing and injecting a sample band. The illustration is based on the simulation results shown in FIG. 17.

FIGS. 8A–8L illustrate a conventional method for producing and injecting a sample band. The illustration is based on the simulation results shown in FIG. 18.

FIGS. 9A–9L illustrate a conventional method for producing and injecting a sample band. The illustration is based on the simulation results shown in FIG. 19.

FIG. 10 illustrates an improved geometry of a junction for producing a thin sample band with reduced bowing of the band.

FIG. 11A illustrates a square junction having a height and width larger than the widths of the channels.

FIG. 11B illustrates a circular junction having a diameter larger than the widths of the channels.

DETAILED DESCRIPTION OF THE INVENTION

Figure 1:
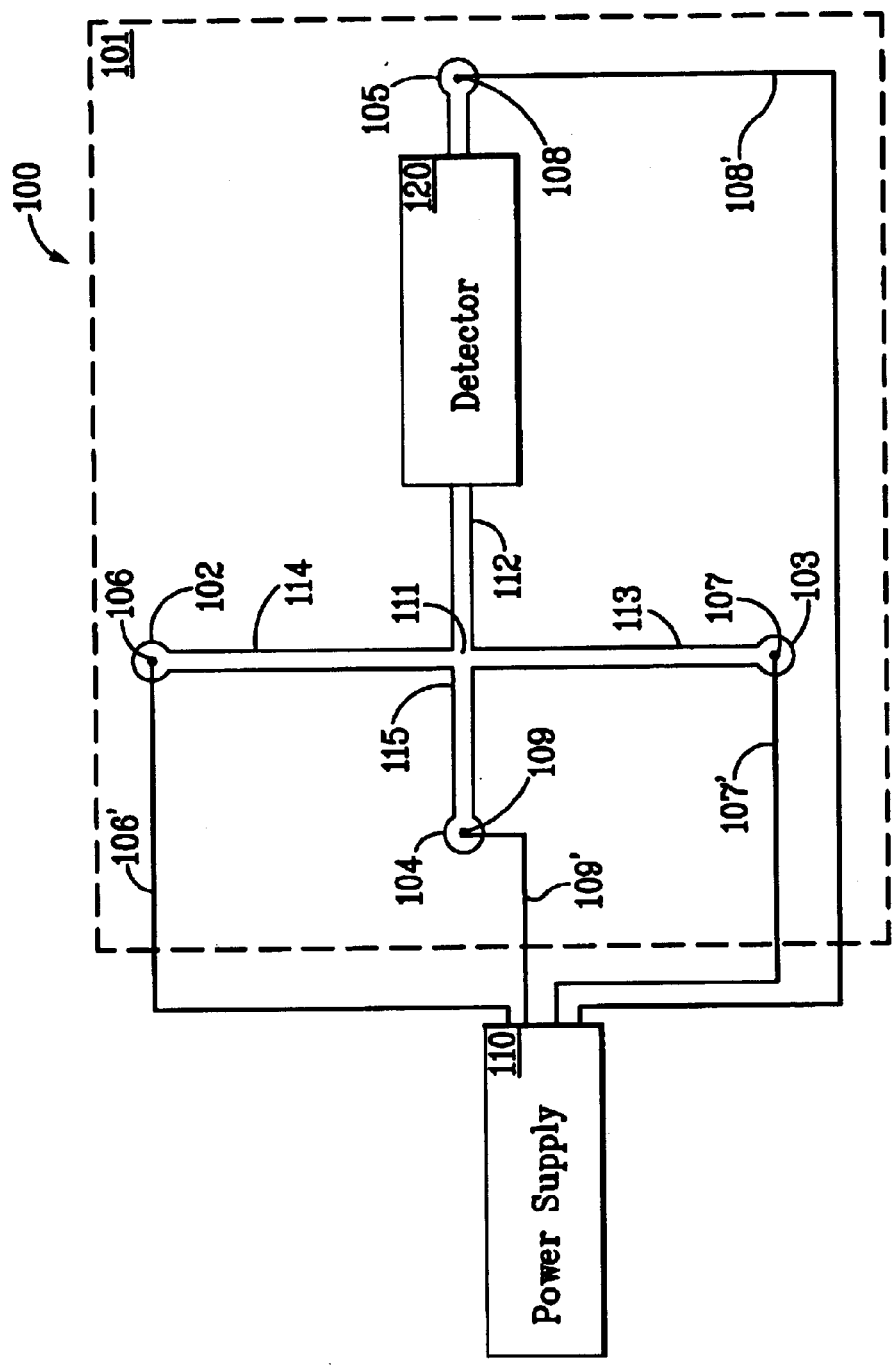
FIG. 1 illustrates a typical prior art channel configuration of a microchannel system used for processing of chemical or biological samples.
Figure 12:
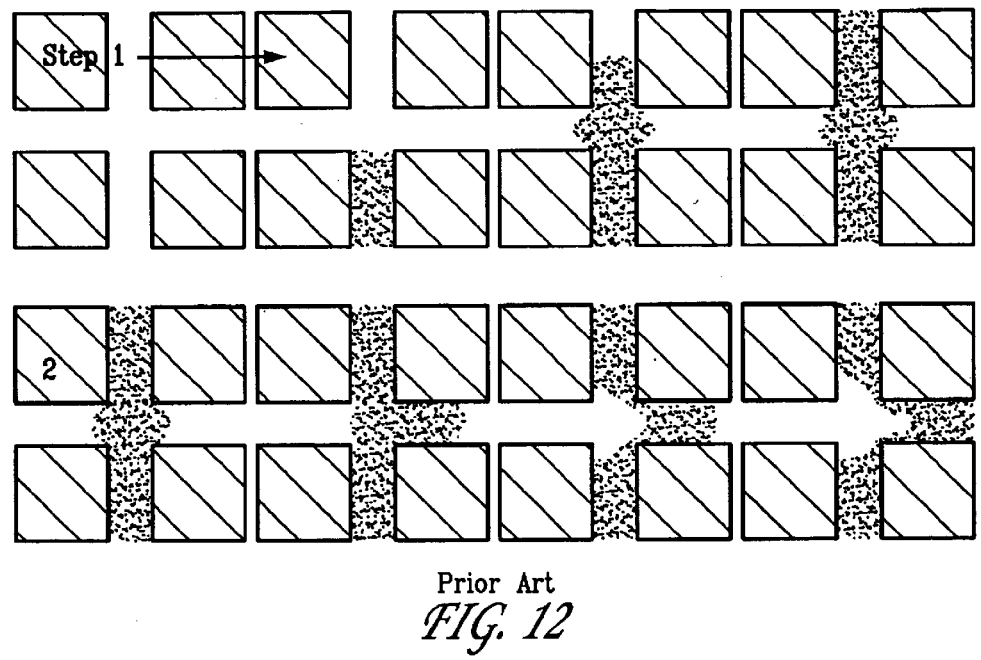
FIG. 12 illustrates graphical output of a computer simulation of a conventional method for producing and injecting a sample band.
Figure 13:
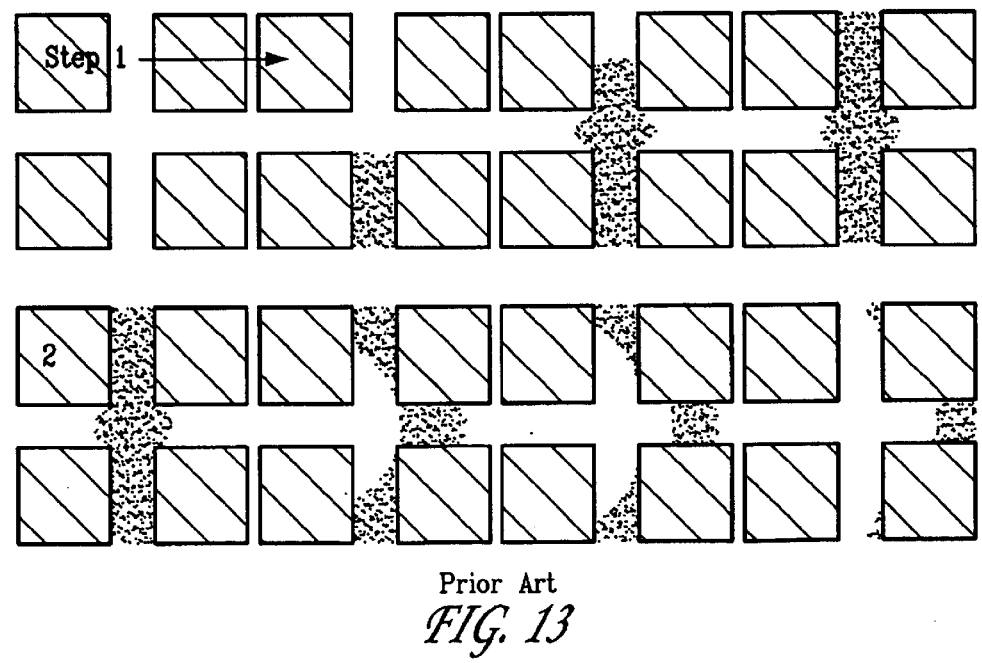
FIG. 13 illustrates the graphical output of a computer simulation of an improved prior art method for producing and injecting a sample band.
Figure 14:
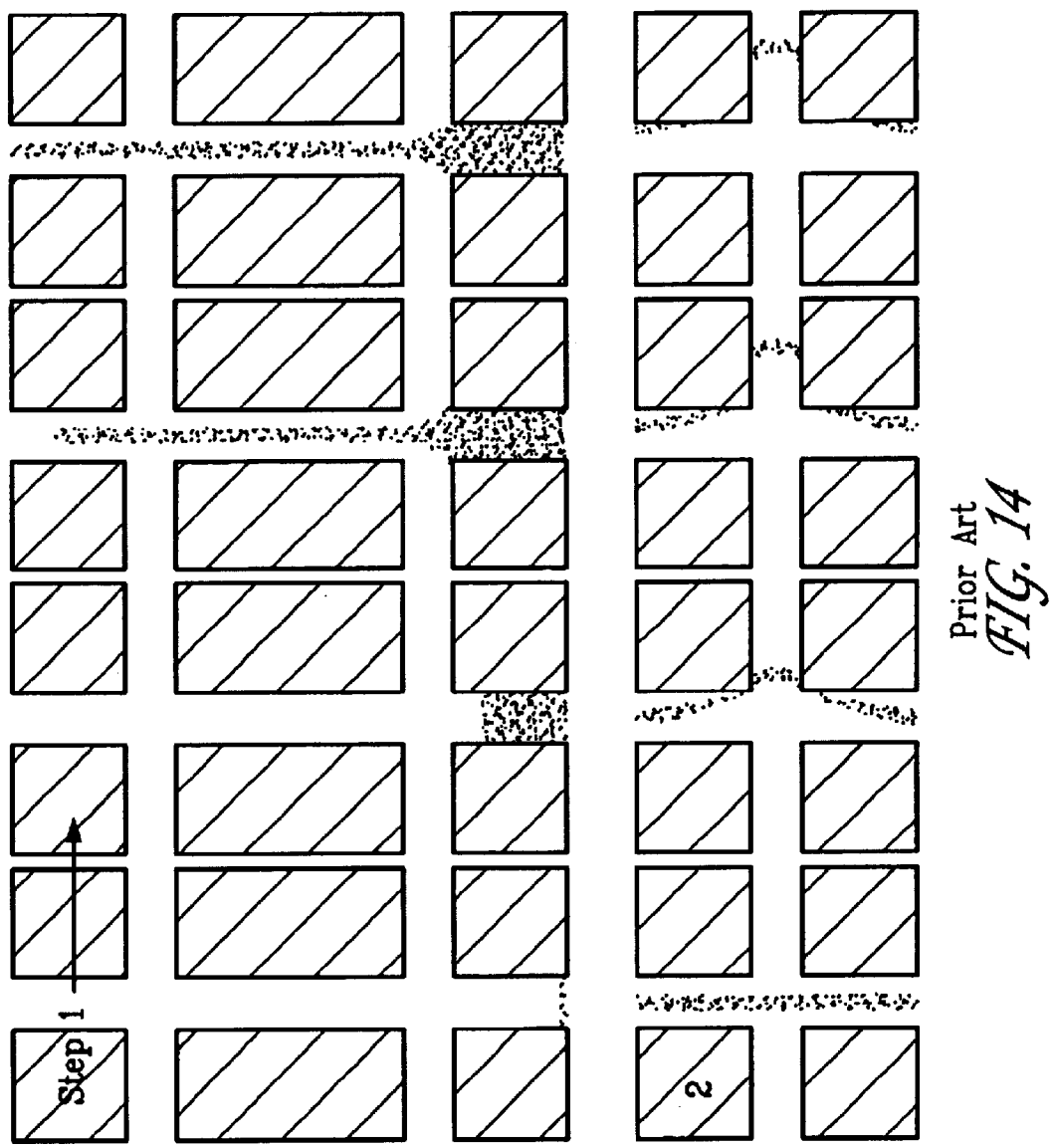
FIG. 14 illustrates the graphical output of a computer simulation of an improved prior art method for producing and injecting a thin sample band by electrokinetic focusing.

The present invention improves the performance of microchannel systems for chemical and biological synthesis and analysis by providing a method and apparatus for producing a thin band of a species sample. Thin sample bands improve the resolution of microchannel separation processes, as well as many other processes requiring precise control of sample size and volume. These improvements are applicable to microfluidic systems employing electroosmotic transport, electrophoretic transport, or pressure-driven flows. The present invention is applicable to all channel depths and to a range of channel cross-sections including, for example, rectangular, trapezoidal and triangular.

Microchannel systems typically include multiple transport channels interconnected with one another and with one or more reservoirs. Such systems may be very simple, including only one or two channels, or may be quite complex, including a great many channels and reservoirs. Here we use the term microchannel system to mean any system having one or more channels. When such systems include reservoirs, the reservoirs can serve both as a means for introducing chemical samples into the system and as a convenient location for electrodes connected to an electric power supply. This power supply is used to apply electrical fields that induce electroosmotic or electrophoretic transport along the channels. Since the transport speed of differing species depends on their adsorption characteristics and relative ratios of ion charge to mobility, microchannel devices are commonly used to perform chemical or biological separation processes. The arrival of separated species peaks or bands is monitored at channel outlets, usually by optical detectors. The timing and intensity of the detector response is then used to infer the composition of the sample under analysis.

Microchannels generally have at least one internal transverse dimension that is less than 1 mm, typically ranging from about 10 μm to 500 μm. Axial dimensions of these microchannels may reach to 10 cm or more. A network of channels and reservoirs is fabricated on a planar substrate by etching, injection molding, embossing or stamping. Lithographic and chemical etching processes developed by the microelectronics industry are now used routinely to fabricate microchannel systems on silicon and glass substrates. Similar etching processes are also used to fabricate microchannel devices on polymeric substrates such as polymethylmethacrylate (PMMA), polycarbonate, polytetrafluoroethylene (TEFLON), polyvinylchloride (PVC), and polydimethylsiloxane (PDMS). However, mass production of microchannel devices is more efficiently performed by stamping, embossing or injection molding of polymeric materials using tools or molds that have been produced by lithography and etching or by electroforming.

After fabricating the microchannel system the planar substrate is usually, but not necessarily, mated with one or more planar sheets that seal channel tops and/or bottoms while providing access holes for injection and extraction ports as well as electrical connections. In all such fabrication processes the channel geometries are initially imprinted by lithographic masks capable of accurately reproducing detailed channel dimensions defined by digital data sets or by scanning images.

Chemical or biological samples are transported through microfluidic devices by electroosmosis, electrophoresis, or by pressure driven flow. In electroosmosis, bulk flow is induced by applying an electric field to a fluid containing a net mobile charge within the Debye layers adjacent to channel surfaces. In electrophoresis, by contrast, there is generally limited bulk motion of the fluid or gel contained within the separation channels. Instead, the applied electric field causes migration of ionic species through a substantially stationary medium, at speeds that depend on the ion charges and mobilities of the species. Both of these processes may occur simultaneously when an electric field is applied to a fluid, though one is usually dominant. In pressure driven flow, bulk fluid motion is induced by applying a pressure difference between channel ends. The present invention is applicable to all electroosmotic and electrophoretic transport processes and to pressure driven flows in devices having channel depths small compared to their widths. Any of these three processes involve species transport along with, or through a fluid, a gel, or a similar material, hereinafter referred to as a transport medium.

To obtain species separation, some portion of the microchannel system may be filled with a separation matrix such as gel or a porous or granular material. Gels are often employed as the stationary phase in electrophoretic separations. Porous and granular materials are often used in chromatographic separations to increase the surface area and provide a specialized adsorption surface known to selectively retard particular species. Alternatively, the separation matrix used to increase surface area may be a small-scale pattern or array of obstacles fabricated within the channel. The selectivity of these fabricated surfaces may also be altered by coating or chemical processing. Thus, to effectively identify the contents of an unknown sample it may be transported simultaneously through multiple separation channels having different separation matrices that selectively adsorb different species. The contents of the sample are inferred from the observed arrival times of separated species bands. Since the measurement resolution depends on physical separation between the bands, it is desirable that the bands be as distinct and sharply defined as possible. Thus starting a separation process with a thin sample band improves the resolution of the separated species bands at the end of the separation column.

Numerical Simulations

Numerical simulations of sample transport in electroosmotic flow are used here to demonstrate the benefit of the present invention over the prior art. The simulations are performed using a computer model written by the inventors specifically for analyzing electrokinetic transport. This model has been benchmarked against direct observation of transport in electroosmotic flows and has been demonstrated to reproduce the experimental results with a very high degree of accuracy. The results of the numerical simulations are presented here, using two different formats: the schematic diagrams of FIGS. 2–9, illustrated as cartoons, and the corresponding computer generated plots of FIGS. 12–19.

The calculations presented here are performed for the limiting case in which the Debye layer thickness is negligible compared to the channel width. This approximation is generally well justified since Debye layers are typically at least 100 times thinner than minimum channel dimensions. Under these conditions the electric field satisfies the Laplace equation, and the induced fluid speed along channel boundaries that are electrically insulating is proportional to the local field strength, in accordance with the Smoluchowski relationship. The velocity field within the channels and junction is computed by solving the full Navier-Stokes equations by means of a stream function and vorticity formulation. Finally, species transport is computed by a Monte Carlo method in which a large number of tracer particles are introduced into the flow and subsequently move by advection and diffusion. The advective transport is computed in a deterministic fashion from the local fluid speed, while diffusive transport is described by a random walk.

Although this numerical model addresses both diffusive and advective transport, diffusion is neglected in the calculations presented here. The relative importance of diffusion and advection is determined by the Peclet number, $P_\theta$.

$$P_e = \frac{ua}{D},$$

and diffusive transport is of secondary importance when the Peclet number is much larger than unity. At a Peclet number of 10, diffusive transport rates are only about 10% of those due to convection. For conditions typical of microfluidic systems, the Peclet number is on the order of 100 based on fluid or ion speeds of u=1 mm/s, a channel width of a=100 μm and a diffusion coefficient of $D=10^{-9}$ m$^2$/s. At a Peclet number of 100, diffusion will spread a sample band by about one channel width during sample transport over a channel length of 100 channel widths. Thus Peclet numbers in microchannel devices must be this large, or even larger, to prevent severe longitudinal sample spreading within long channel runs. As such, diffusive transport is appropriately neglected in the processes discussed here since we are interested only in transport over a few channel widths. The only exception to this is cases in which the sample band becomes very thin compared to the channel width. Even in these cases, diffusion may be neglected provided that the Peclet number is suitably large.

In all of the example calculations presented here the sample material consists of neutral species that are transported by electroosmotic flows induced by applied electric fields. However, the computed sample band transport is equally descriptive of electrophoretic transport of charged sample species through a stationary transport medium. It is also descriptive of sample transport by any combination of these two electrokinetic mechanisms. This equivalence holds true provided that the Debye layer is thin compared to the transverse channel dimensions and there are no applied pressure gradients, as is typical of practical microchannel devices. Under these restrictions and a few lesser assumptions, both of the basic electrokinetic transport processes induce sample transport along current flux lines and the transport speed is proportional to the magnitude of the local electric field. In electroosmosis this transport speed is the bulk fluid speed while in electrophoresis it is the ion drift speed relative to the transport medium. When both mechanisms occur simultaneously, the speed of a particular ion species is the sum of the electroosmotic and electrophoretic components, which is still simply proportional to the applied field.

The present invention provides new methods for producing a sample band for subsequent processing in a microchannel device, such that the thickness of the sample band is small and where only a single microchannel junction is employed; no auxiliary junctions are required. The invention also provides a means for controlling the thickness of the sample band without altering the junction or channel geometry.

These new methods comprise a series of steps in which the sample is manipulated within the junction and the channels that intersect the junction. The required sample manipulations can be performed using conventional channel and junction geometries. In this case, the method is readily implemented by programming a power supply to perform the required steps of applying electric potentials to reservoir electrodes or, equivalently, of imposing electric currents along some or all of the channels intersecting the junction. Alternatively, the same sample manipulations may be performed in improved junction geometries, providing still further reductions in the thickness of the resulting sample band.

In describing the new methods, it is convenient to sequentially number each step in the process of sample manipulation. At the onset of a given step an electric field is applied and held substantially fixed until it is removed at the end of the step. Of course it is possible to achieve the same final result using time varying electric fields.

In each of the first three embodiments described below, the series of steps may be grouped into two composite processes: (1) insertion, wherein an initial sample band is formed or placed within one of the primary channels or within the junction near one of the abutting channel ends, and (2) sample thinning, wherein the initial sample band is reduced in thickness. The resulting sample band is injected into the process channel at the end of the last thinning step. Each of the two composite steps, insertion and thinning, may be performed in a number of different ways, as illustrated by the first three embodiments below. In these first three embodiments, the first two steps are used for sample insertion, the remainder for thinning. These embodiments are only intended as illustrative examples of how two new building-block procedures, one for insertion and one for thinning, can be used in conjunction with one another and with other prior art procedures.

To simplify the discussion that follows it is assumed that an applied electric field produces current flow and sample band transport from regions of high electric potential to regions of lower potential. As noted earlier, the direction of electrokinetic transport relative to the applied field depends upon the sign of the Zeta potential in an electroosmotic flow or the sign of the ion charge in electrophoresis. In cases where transport occurs from low to high potential (opposite to the direction assumed here), the desired transport may be induced by applying potential differences or electric current flows that are opposite to those stated below.

Figure 15:
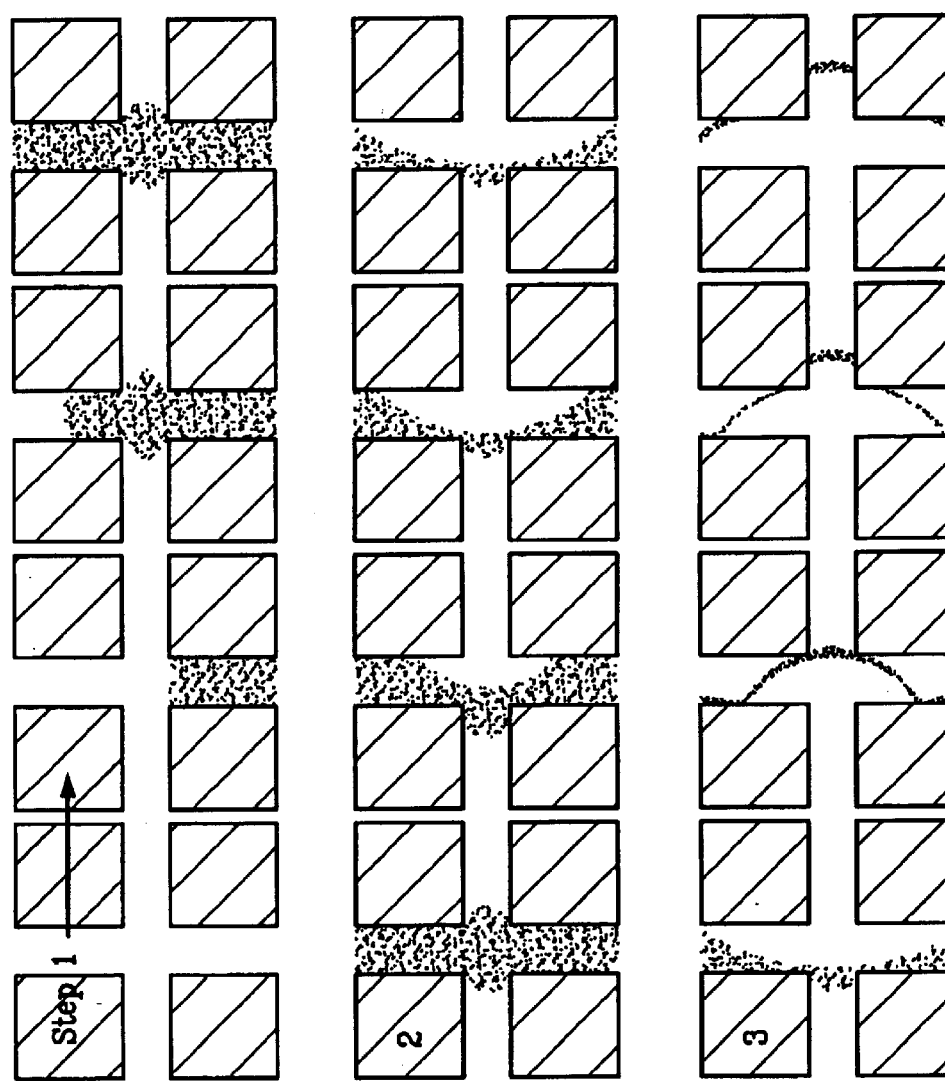
FIG. 15 illustrates the graphical output of a computer simulation of the first embodiment of the present invention.
Figure 16:
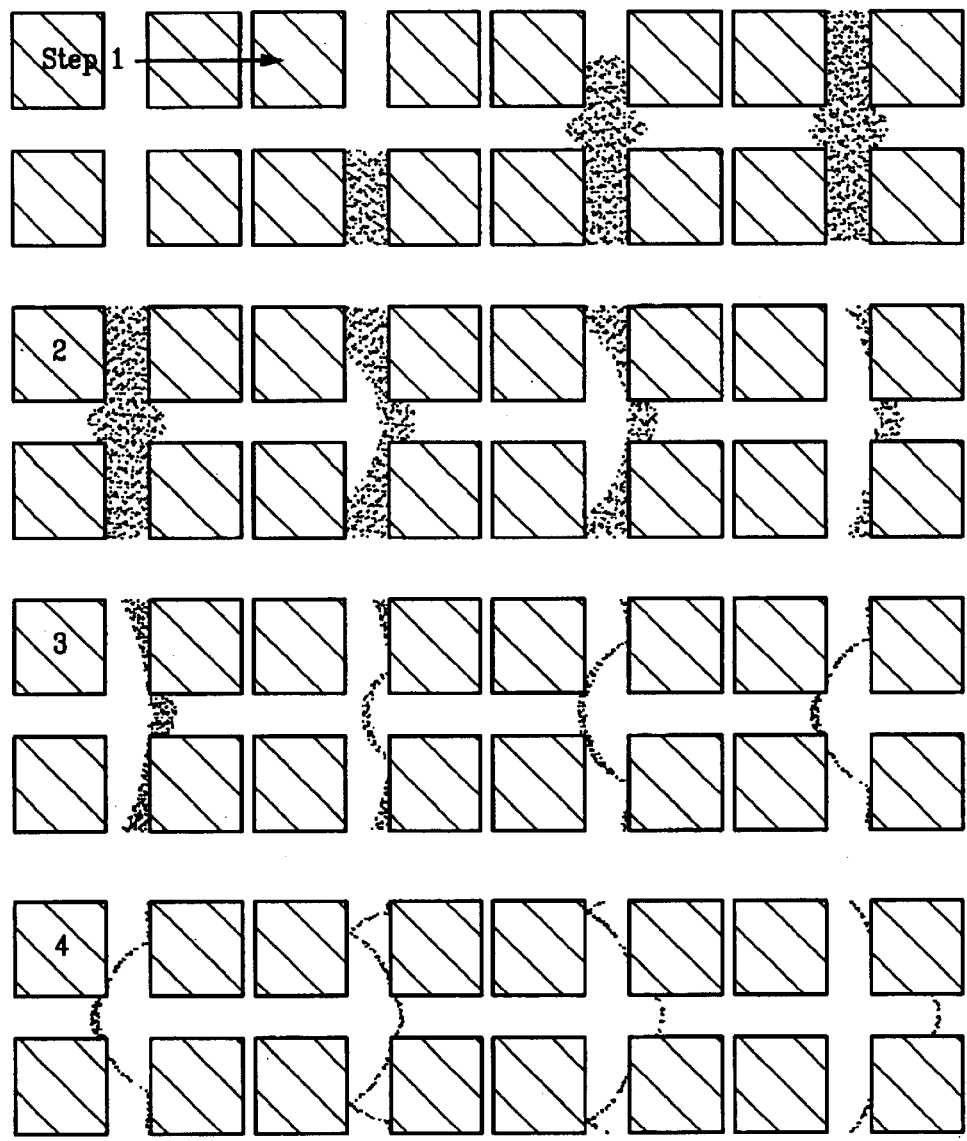
FIG. 16 illustrates the graphical output of a computer simulation of the second embodiment of the present invention.

Embodiment One:

The fundamental concept of the present invention is illustrated schematically in FIGS. 5A–5L (also shown as a computer simulation plot in FIG. 15). In this first embodiment, the sample manipulations required to produce the sample band comprise a series of three steps. In the first two steps an initial sample band is inserted into one of the primary channels, here the supply channel. In the last thinning step, the thickness of this initial sample is reduced and it is injected into the process channel.

(1.) The first step, shown in FIGS. 5A–5D, is the same as the first step shown previously in FIGS. 2 and 3: sample material 206 is transported through supply channel 204 until it fills junction 205 and continues to flow toward the waste reservoir (not shown) through waste channel 201. This step produces an initial sample volume in the junction 205 that intrudes about one channel width into the buffer and process channels 203 and 202, respectively to the left and right of junction 205. This is illustrated in the distinctive side lobes 207 of FIGS. 2C, 3C, and 5C. Again, as with FIGS. 2 and 3 the last frame of the first step, FIG. 5D, is identical to the first frame of the second step, FIG. 5E.

(2.) In the second step, unique to the present invention, the sample volume near junction 205 is reduced, leaving an initial sample band in the channel opposite to the process channel 202. To obtain this result, the electric potential of the process channel reservoir (not shown) is elevated above that of the supply and waste channel reservoirs (not shown), thereby inducing transport from process channel 202 toward junction 205 and out through supply and waste channels 204 and 201 away from junction 205. There is little or no sample transport along buffer channel 203 during this step. Transport along buffer channel 203 can be prevented simply by opening the connection between the power supply and the buffer electrode, permitting the buffer electrode potential to "float" at the junction potential. Alternatively, the current in this channel may be controlled to be zero by using an appropriate power supply. The electric currents in the other three channels can also be controlled to provide the desired sample speeds. Note that this step is not equivalent to the Step 2 shown earlier in FIGS. 3E–3H since that step involved simultaneous transport along all four channels abutting junction 205. Here, the absence of sample transport in the buffer channel means that the buffer channel 203 retains the left-most portion of the sample lobe 207 extending into buffer channel 203. The remainder of sample material is removed by the prevailing transport through supply and waste channels 204 and 201. The retained volume of sample material 207', comprising most of the left lobe 207, in buffer channel 203, now forms the precursor of a sample band 207', a portion of which will be later transported across the junction into process channel 202 to produce the final sample band $200_5$. It is also important to note that by increasing sample speeds during this second step or by increasing the duration of the transport through supply and waste channels 204 and 201, the volume of the precursor sample band 207' is reduced which has the effect of also reducing the thickness, d, of the injected sample band $200_5$. Likewise, the opposite is true: reducing the speeds or duration of the transport through supply and waste channels 204 and 201 increases the retained sample volume 207' and so will increase the thickness of injected sample band $200_5$.

(3.) In the third and final step, illustrated in FIGS. 5I–5L, the initial sample band 207' that has been produced within the buffer channel 203 is thinned by transporting it across junction 205 toward the process channel 202 while also extracting portions of the sample band 207' into the supply and waste channels, 204 and 201. As with the relationship between the first and second steps of FIGS. 2 and 3, the last frame of the second step FIG. 5H is identical to the first frame of the third step FIG. 5I. During this step, the applied electric fields are similar to those used in FIGS. 3E–3H (Step 2): the electric potential in the buffer channel reservoir (not shown) is raised above that in the reservoirs terminating the supply, waste and process channels (not shown). This step is not, however, equivalent to that previous procedure because it is not used here to create an initial sample band as in the prior art. Instead, the present method uses the diverging transport field within the junction 205 to reduce the thickness of a sample band 207' that has already been formed in steps (1) and (2) above and positioned to take maximum advantage of the diverging transport field induced during this final step. Since the starting position of the sample band 207' is now to the left of the junction 205, rather than actually within junction 205, a portion of the sample is carried away from the junction into the supply and waste channels 204 and 201. This occurs because as sample band 207' leaves buffer channel 203 and traverses junction 205, the radial divergence of the transport field leaving the buffer channel stretches the sample band, further thinning the sample before it enters the process channel. This method of using a divergent transport field to stretch and thin a sample band is a unique aspect of the present invention. The end result of this three-step process is a sample band $200_5$ having a thickness equal to about one-third of the channel width.

The above first embodiment of the invention produces a sample band comparable in thickness to the most sophisticated level of prior art shown earlier in FIGS. 4A–4H, yet the present method achieves this superior performance without additional channels, junctions, reservoirs or controller outputs. This new method can thus be applied to existing separation or processing devices. In addition, the present method can be extended to produce sample bands of still smaller thickness by executing an additional series of sample manipulations using the same single junction and the same minimal set of hardware. These are described below.

Embodiment Two:

FIGS. 6A–6P illustrate a four step second embodiment of the present invention. Shown is a more involved version of the basic method of the present invention. The four-step sequence of FIG. 6 is nearly identical to that shown in FIGS. 5A–5L but includes one additional step which is essentially a repetition of the thinning step shown in FIGS. 5I–5L. The second embodiment of FIG. 6 differs in one other respect from the first embodiment of FIG. 5: the direction of motion along the primary channel has been reversed at each step so that the final direction of sample motion is the same as before.

The new four-step process illustrated in FIGS. 6A–6P proceeds as follows:

(1.) As before, sample material 206 is transported through supply channel 204 until it fills junction 205 and continues to move toward the waste reservoir (not shown) through waste channel 201. This step produces an initial sample volume near junction 205 that again intrudes about one channel width into the buffer and process channels 203 and 202, respectively, to the left and right of junction 205, forming the distinctive lobes 207 of FIGS. 2C, 3C, 5C and 6C.

(2.) The second step of the process, FIGS. 6E–6H, is identical to the second step of the first embodiment, FIGS. 5E–5H, except that the direction of sample transport along the buffer and process channels 203 and 202 is reversed so that the initial sample band 207' is produced at the process channel 202 rather than the buffer channel 203. To obtain this result, the electric potential of the buffer channel reservoir (not shown) is elevated above that of the supply and waste channel reservoirs (not shown), such that the current flow and sample transport are directed along buffer channel 203 toward junction 205 and out through supply and waste channels 204 and 201 away from junction 205. As with the first embodiment, there is little or no current flow or sample transport along process channel 202 in this step. At the end of this step, a retained sample band 207' is thus positioned in or near the head of the process channel 202. This is just opposite the position of sample band 207' in the first embodiment. However, the sample distribution is otherwise the same.

(3.) The third step is a thinning step in the process, FIGS. 6I–6L, in which sample band 207' is transported across junction 205 by raising the electric potential in the process channel reservoir (not shown) relative to that of reservoirs terminating the supply, waste and buffer channels (not shown). Again, a fraction of the sample is carried away from the junction into the supply and waste channels 204 and 201. As before, the radial divergence of the transport field leaving the process channel stretches and thins the sample band. This stretching reduces the thickness of sample band 207' to produce a substantially thinner sample band 207".

At the end of this step, FIG. 6L, the sample geometry is the same as that shown in the middle frames of the third step, FIGS. 5J and 5K, except that a thinned sample band 207" is now positioned on the opposite side of junction 205. Also note that in the current embodiment, the thinned sample band is not injected into buffer channel 203 but is instead arrested just as the thinned band 207" nears buffer channel 203.

(4.) The fourth and final step of the present embodiment, FIGS. 6M–6P, is a duplication of Step 3 of the first embodiment illustrated in FIGS. 5I–5L. Sample thinning is performed by raising the electric potential in the buffer channel reservoir (not shown) relative to that of the reservoirs terminating the supply, waste and process channels (not shown). This has the effect of inducing current flow and sample transport along buffer channel 203 into junction 205 and out through the process, supply, and waste channels, 202, 204, and 201. Furthermore, since the starting position of the thinned sample volume 207" is now located at buffer channel 203, another fraction of sample 207" is again carried away from the junction into the supply and waste channels 204 and 201 due to the divergence of the transport field leaving the buffer channel. The result of this enhanced method is a sample band $200_6$ exhibiting a greatly reduced thickness, d, relative to the basic method.

The use of multiple thinning steps, even beyond the two steps illustrated above, can be used sequentially to reduce the sample band to a thickness that provides an optimal balance between resolution and detectability. In the absence of diffusion, the thinning process disclosed here does not reduce species concentrations within the sample. This holds true in electroosmotic flows, since the divergence of an incompressible flow cannot change the overall sample volume or species concentration. Only the geometry of the sample volume is affected. The same is true of electrophoresis as well as electroosmosis; neither process reduces sample concentrations. In either case, if transport speeds during thinning are sufficiently high, and if little time elapses between each step, then the sample band may be reduced very substantially by repeated thinning before diffusive transport has a significant detrimental effect in broadening the sample band.

Figure 17:
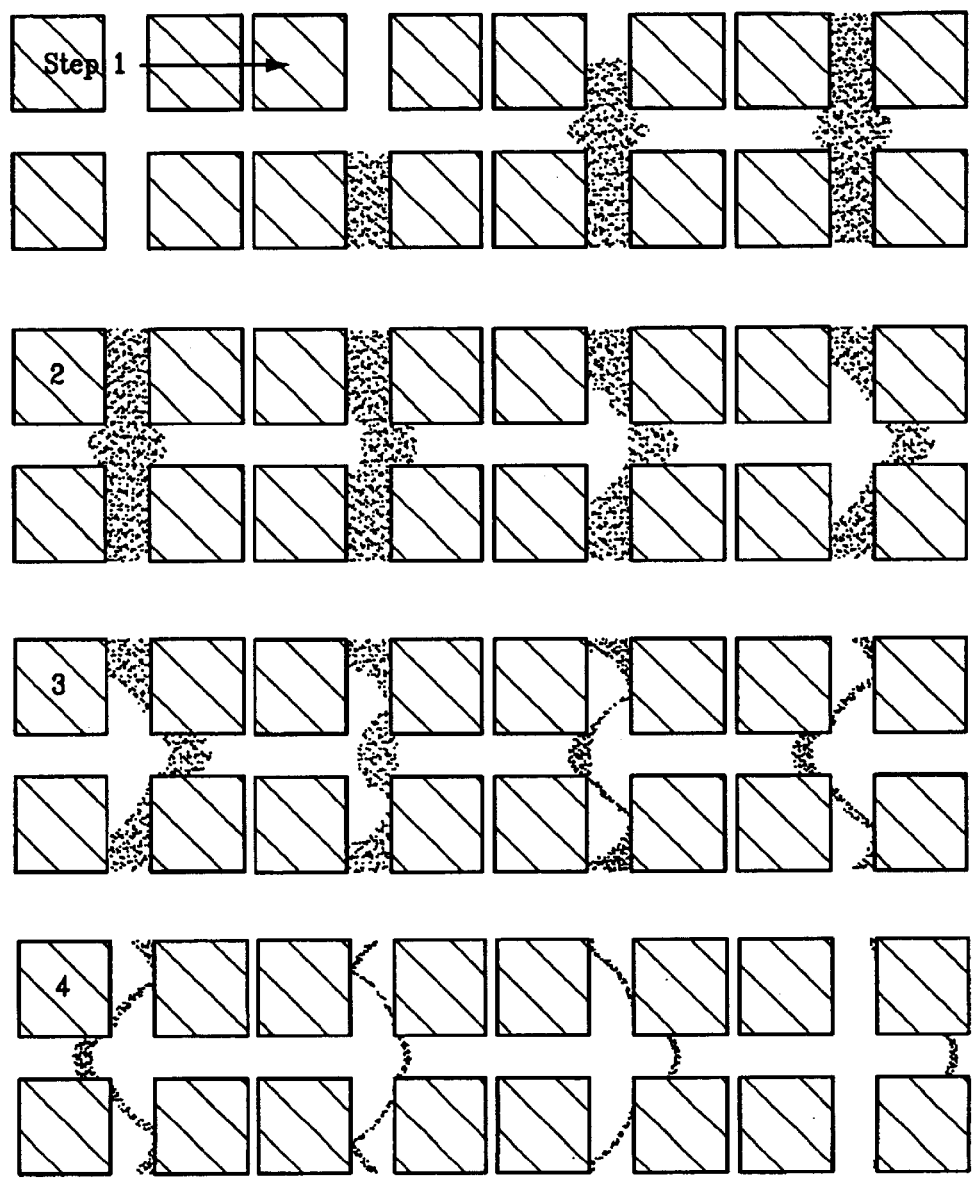
FIG. 17 illustrates the graphical output of a computer simulation of the third embodiment of the present invention.
Figure 18:
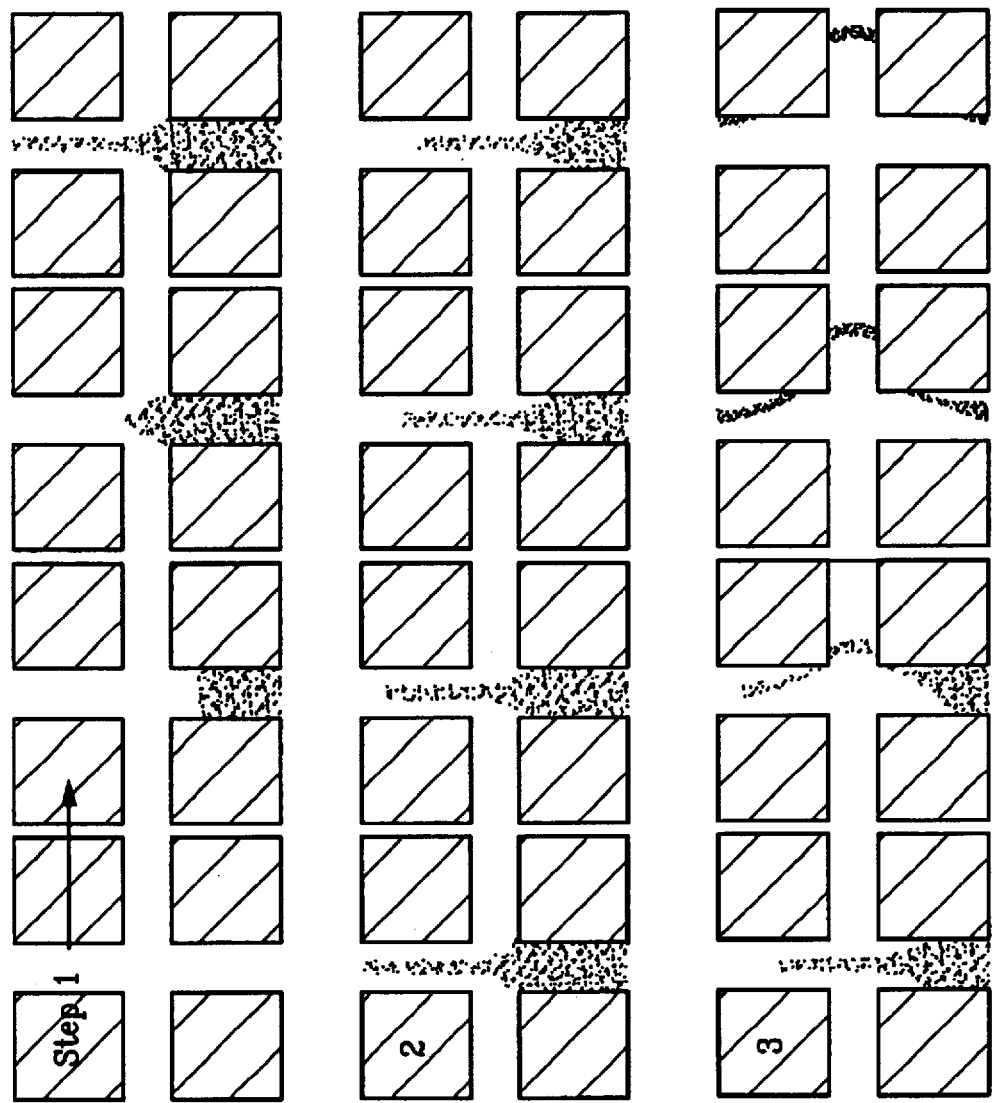
FIG. 18 illustrates the graphical output of a computer simulation the fourth embodiment of the present invention.

Embodiment Three:

A third embodiment of the present invention is schematically illustrated in FIGS. 7A–7P, and depicted in a corresponding computer simulation shown in FIG. 17. Here, the initial sample band is formed by the method illustrated earlier in FIGS. 3A–3H, rather than the improved method illustrated in steps 1 and 2 of FIGS. 5A–5H and 6A–6H. This is followed by application of two thinning steps, similar to those illustrated in FIGS. 6I–6P. These thinning steps, unique to the present invention, can be used to post-process an existing sample band produced by any method, or to re-thin a sample band that has already been subjected to previous processes.

This third embodiment provides a process for thinning a sample using two (2) thinning steps. As stated, the first set of frames in FIGS. 7A–7D is identical to those depicted in FIGS. 3A–3D. In the second step, shown in FIGS. 7E–7H, the applied fields induce transport from buffer channel 203 through junction 205 into the process, supply, and waste channels 202, 204 and 201. This second step forms sample band $200_7$, similar in nature and size as band $200_3$ as shown earlier in FIG. 3F, except that the resulting sample band $200_7$ is transported only to a region near or just into process channel 202.

The direction of sample transport is then reversed right-to-left in a third step, FIGS. 7I–7L. In this thinning step, current flow and sample transport is directed from process channel 202 through junction 205 into the buffer, supply, and waste channels 203, 204 and 201. This step results in a thinner sample band $200_7$. Each of these thinning steps reduces the sample band thickness by about a factor of three or four. The final step, FIGS. 7M–7P, is a thinning step directed toward the process channel 202, resulting in sample band $200_7''$ that may be further transported along the process channel 202, FIG. 7O. The benefit of this approach is that it is quite insensitive to the applied potentials and relative transport speeds, provided that reasonable top-to-bottom symmetry is maintained. Even if the sample band is transported well into a channel during one or more of the thinning cycles, this does little or no harm since the sample profile is not much altered once the band is within the channel. Note that repeated thinning steps do not increase the bow of the sample profile since the bowing induced by each single thinning step is just offset by each subsequent thinning step.

Embodiment Four:

A fourth embodiment of this invention, illustrated schematically by FIGS. 8A–8H, differs significantly from those already discussed. Again, the illustrations of FIG. 8 are based on a computer simulation graphically shown in FIG. 18. Rather than thinning the sample band by stretching the sample band within the junction, this last method employs sample focusing similar to that illustrated in FIGS. 4A–4H. However, in the present invention, focusing is performed within a single junction 205 using a three-step process that does not require the use of the additional junction seen in FIGS. 4A–4D, and the additional hardware previously described as part of the FIG. 4 prior art device. To focus a sample 200 within the junction 205 by means of the present invention, the junction is first filled from the supply channel 204 in the presence of simultaneous current flow into junction 205 from both the buffer and process channels 203 and 202, FIGS. 8B and 8C. This leaves a focused portion 206' of sample stream 206 in the waste channel 201, and with the supply channel 202 completely filled. Such asymmetry between the top and bottom would lead to injection of a long and a lopsided band into the process channel. To avoid this, a second step, FIGS. 8E–8H, is taken in which an electric field is applied along the waste and supply reservoirs (not shown) to induce sample transport in the direction OPPOSITE to Step 1. This moves the focused sample 206' downward into and through the junction, and results in a sample distribution like that shown in step 2, FIG. 4E. During this second step the current flow and transport in the buffer and process channels 203 and 202 may be held static or, alternatively, directed into junction 205 to further thin the sample. As with the methods employing multiple thinning steps, Steps 1 and 2 of this method may be repeated multiple times to further thin a sample volume 206' prior to injection. The final step in this method, FIGS. 8I–8L, transports a portion of the focused sample stream 206' across the junction 205 into the process channel, thereby producing the final sample band $200_8'$. This may be performed by raising the potential in the buffer channel reservoir above those in the other three reservoirs.

Figure 19:
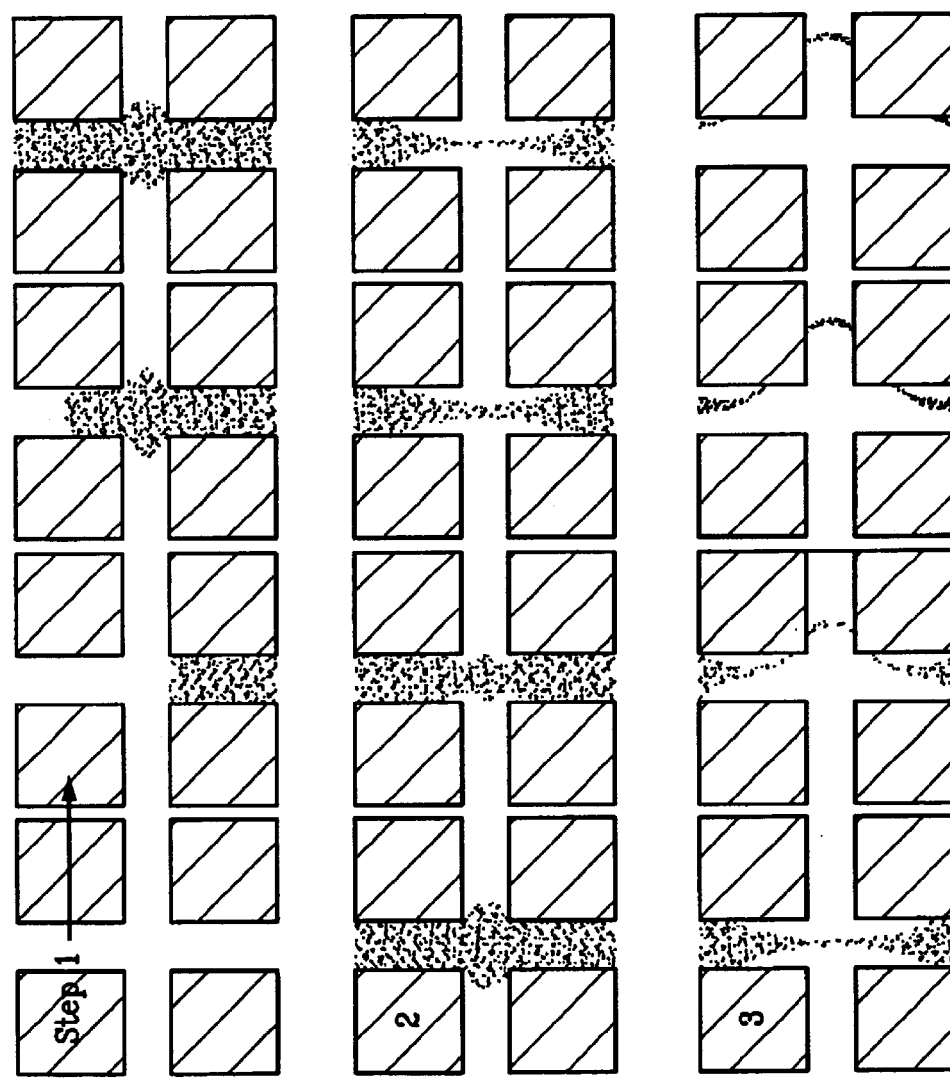
FIG. 19 illustrates the graphical output of a computer simulation of the fifth embodiment of the present invention.

Embodiment Five:

A fifth embodiment of the present invention is illustrated schematically in FIGS. 9A–9L, which is based on the computer simulation shown in FIG. 19. As in the preceding fourth embodiment, sample thinning and injection is performed using a single junction. However, rather than using a focusing step as a part of the thinning process, the fifth embodiment uses an-axial stretching-process unique to the present invention.

The first step in this new stretching and injection process is simply the familiar filling of the junction by transport of sample material from the supply channel 204 into the waste channel 201, as seen in FIGS. 9A–9D. In the second step, shown in FIGS. 9E–9H, current flow is directed from the buffer and process channels, 202 and 203, into the junction and out through the supply and waste channels. As a result, the band of sample material 220 remaining within the junction is axially stretched and thinned. In the example shown, the nearly identical current flows from the buffer and process channels produce a thinned sample that is centered within the junction. A moderate imbalance of these currents would simply shift the stretching band off of the center of the junction. The sample band 220 continues to stretch as long as the electric fields are applied so the sample can be easily thinned to any desired final thickness. The third and final step of the fifth embodiment, FIGS. 9I–9L, provides injection of the stretched sample into process channel 203. This is done here by raising the potential in the buffer channel above that in the other three channels, thereby injecting the final sample band $200_9'$ into the process channel.

The axial stretching process used in the second step of this fifth embodiment is not equivalent to prior art sample focusing processes illustrated in FIG. 4. In sample focusing, current flows into the junction from three channels and out through one. In the prior art configuration, a focused sample stream of reduced thickness flows away from the junction along a single outflow channel. In contrast to that prior art, axial stretching involves opposing current inflows along two coaxial channels coupled with opposing outflows along the other two coaxial channels. This new process produces a progressive thinning of the band of sample material that remains centered within the junction.

Axial sample stretching has several advantages over prior art. Only one junction is required for both stretching and injection. The process only involves three steps in which current flows within the system are altered. Any desired sample thickness can be produced by simply controlling the duration of the stretching step. Finally, at the end of stretching step, the sample stream is already positioned for immediate injection into the process channel.

Apparatus

All of the embodiments illustrated thus far have employed supply, waste and buffer channels having the same width as the process channel. This is not necessary to employ these methods, and indeed certain improvements may be had by increasing or reducing the width of these channels relative to the width of the process channel. For example, increasing the width of the supply and waste channels relative to the buffer and process channels increases the volume of the junction. This larger volume yields a more pronounced thinning of the sample volume each time it is transported across the junction. However, this also tends to produce more significant bowing of the sample band finally injected into the process channel. Thus a trade-off is involved in selecting the widths of the supply, waste and buffer channels relative to that of the process channel. The benefits and detriments of this trade-off determine the preferred ratios of the channel widths for any specified application. Similarly, reducing the widths of the supply and waste channels relative to the process channel provides less thinning of the sample volume on any given traverse of the junction, but also yields a sample band that is flatter across the process channel. Overall we have found that channels of equal size provide a reasonable balance between these competing effects, but that channels of unequal size may provide some benefit in special cases.

Sample manipulation in a conventional junction, as illustrated here, is very effective in reducing and controlling the thickness of the resulting sample band. However, as the sample volume is increasingly thinned, the resulting band thickness becomes dominated by the bow of the band just before it enters the process channel. The origin of this bow is the fact that sample speeds near the walls of the process channel and adjacent to the junction are reduced from the centerline values due to nearby transport into the supply and waste channels. One means to eliminate these local regions of low transport speed is to reduce the overall transport into the supply and waste channels. However, such transport is desirable for minimizing tails on the resulting sample band and provides the radial divergence of the transport field necessary for the effective sample thinning. A better approach is to alter the geometry of the junction in the vicinity of the process channel to reduce the influence of the supply and waste channels on speeds near the process channel. Such a geometry is shown in FIG. 10.

The apparatus of FIG. 10 illustrates one embodiment of the present invention in which cusp-like extensions 300 to the process channel walls 202$_1$ protrude into junction 205. The benefit of extensions 300 is to increase transport speeds along the process channel walls 202$_1$ in the vicinity of junction 205, and thereby reduce the bow induced in the sample band 200. The geometry shown is intended primarily for use with the basic three-step method illustrated in FIG. 5. It is understood in the context of the various new methods described above that such cusp-like extensions may also be beneficial when used on one or more of the supply, waste and buffer channels.

In addition to the specific geometry shown in FIG. 10, there are a number of other modifications of the junction geometry that can be used to alter the tradeoff between sample thinning and sample bowing. An increase in the plan-view area of the junction relative to the widths of intersecting channels will tend to increase the divergence of a sample band as it is transported from an inlet channel through the junction into the outlet channels, providing the benefit of a greater reduction in sample thickness. For example, the rectangular junction of FIG. 11A and the circular junction of FIG. 11B both have plan-view dimensions that are greater than the widths of the intersecting channels. In these geometries, however, portions of the sample band traveling along the junction walls will reach the outlet channels later than the portions that travel directly through the center of the junction, increasing the bowing of the final sample band. Such increases in bowing can be overcome to some extent by detailed optimization of the junction geometry and by stronger withdrawal of sample material through the side branches.

Junctions having plan-view dimensions smaller than the nominal widths of the connected channels (not illustrated) can also provide benefit. Such geometries can be realized by tapering the widths of the channels as they approach the junction. The sample manipulation procedures of the present invention can then be performed at the reduced scale of a smaller intersection of narrower channels. Since the thickness of the resulting sample band is proportional to the width of the channels adjacent to the intersection, the thickness of the resulting sample band will be smaller at the reduced scale. At the end of the sample manipulations, the resulting sample band may be transported through a process channel that expands in width back to nominal the channel width used to perform subsequent processes. Since the transport field diverges along an expanding channel, the sample will be still further thinned during transport along the expanding channel segment. One drawback of this approach is that additional sample bowing generally occurs during transport through an expanding channel, particularly if the expansion angle is steep. Another disadvantage is that constriction of the electric field in the vicinity of the junction causes increased joule heating of the transport medium. These disadvantages must be weighed against the advantages of a reduced junction size.

All of the examples shown here address the most common case of channels and junctions having a uniform depth. This choice is made because this is the most easily fabricated and commonly used configuration in the prior art. Also, electrokinetic sample transport in such an apparatus is strictly two-dimensional and is not influenced by the channel depth, provided that the depth is uniform and the Debye layers are thinner than the lateral channel dimensions. However, the basic processes of sample manipulation disclosed here can also be performed in an apparatus having nonuniform channel depths. Such devices would offer further opportunities for sample thinning by flow divergence in three rather than two dimensions.

Similarly, all of the examples shown here address the case in which the channels of a microchannel system all lie in a common plane, since this is the most straight-forward configuration to describe and fabricate and thereby to actually reduce to practice. However, the methodology and apparatus disclosed and illustrated in these two-dimensional planar networks can be easily extended to three-dimensional networks in which a junction can be formed by the intersection of six channels with four of these lying in a common plane and the other two lying in an orthogonal plane. Such devices offer the opportunity for sample thinning by divergent flow in three rather than two dimensions.

Finally, those skilled in the art will recognize that this same approach is just as easily extended to more complex networks containing more than six channels wherein one or more channels form non-orthogonal angles with each other.

The present invention and the illustrative calculations presented here are applicable not only to transport by electroosmotic flow and by electrophoresis but also to some pressure driven flows. To establish this range of application, it is first noted that the vorticity in an electroosmotic flow is everywhere zero under fairly general conditions, regardless of the channel geometry. The main requirements are that there are no applied pressure gradients, that the Debye layers be thin compared to transverse channel dimensions, and that the fluid properties and properties of the channel boundaries are everywhere the same. The geometry of the channel or channels need not be restricted in any way. Under these conditions, the fluid motion is a potential flow and the fluid velocity is uniformly proportional to the applied electric field. In this regard an electroosmotic potential flow is completely analogous to electrophoretic species motion. It is therefore understood that methods and channel geometries that are beneficial for producing thin sample bands via electroosmotic flow are also beneficial via electrophoretic motion. Moreover, these methods and apparatus are also applicable to channels filled with a porous or granular solids since the presence of these elements does not alter channel-scale transport in potential flows. Pressure-driven flows in wide shallow channels and in channels filled with a separation matrix such as a porous or granular material may also be potential flows. For these special cases, the present methods and apparatus are also applicable to flows driven by applied pressure gradients.

Finally, the new methods of sample manipulation described here can be used to improve the performance of microfluidic devices even in cases where the restrictions outlined above, such as thin Debye layers, may not be well satisfied. In those instances, the methods still function in the same qualitative manner, but the results may differ quantitatively from those depicted in the illustrative numerical simulations.

What is claimed is:

1. A method for producing a thin sample band in a microchannel system, said method comprising the steps of:
   a.) forming a junction at an intersection of at least four channels, wherein each of said channels has a first end contiguous with said junction and a second end opposite said first end, wherein each of said channels lie in a substantially common plane, wherein first and second channels are substantially co-linear and disposed along a primary axis, and wherein third and fourth channels lie on opposite sides of said primary axis;
   b.) filling each of said channels and said junction with a transport medium, wherein said channels, and said junction are all in communication with each other, and wherein said transport medium filling said third channel comprises a quantity of a sample material comprising one or more species;
   c.) applying first electric fields along said third and fourth channels in order to induce transport of some of said sample material along said third channel and into said fourth channel and filling a region of said first and second channels adjacent to said junction with portions of said sample material;
   d.) removing said first electric fields;
   e.) applying second electric fields along said second, third, and fourth channels thereby transporting a portion of said sample material out of said junction and said second channel first end and into said third and fourth channels, wherein a band of said sample material remains in said first channel first end proximate said junction;
   f.) removing said second electric fields;
   g.) applying third electric fields along said first, second, third and fourth channels wherein said sample band in said first channel first end is transported into said junction, said transport causing said sample band to expand into said junction toward said second, third and fourth channels wherein end portions of said sample band enter said third and fourth channel first ends thereby causing said sample band to be stretched and thinned while traversing said junction, and wherein a center portion of said sample band is disposed in a region proximal to said second channel first end; and
   h.) removing said third electric fields.

2. The method of claim 1, wherein said first, second, and third electric fields produce electroosmotic motion of said transport medium thereby causing said sample band to be carried along with said transport medium.

3. The method of claim 1, wherein some of said species comprise ionic species and wherein said first, second, and third electric fields produce combined electroosmotic motion of said transport medium and electrophoretic motion of ionic species within said sample band thereby causing said sample band to move with, and relative to, said transport medium.

4. The method of claim 1, wherein the transport medium is substantially stationary.

5. The method of claim 4, herein said species comprise ionic species and wherein said first, second, and third electric fields produce electrophoretic motion of said ionic species relative to said transport medium thereby causing motion of said sample band through said channels and junction.

6. The method of claim 1, wherein said channel second ends are each connected to separate reservoirs, wherein each of said reservoirs include electrodes connected to an electrical power supply, said power supply used to control said electric fields along each of said channels.

7. The method of claim 1, wherein the step of applying third electric fields produces transport of equal portions of said sample band into said third and fourth channels wherein said sample band remains symmetric about said primary axis.

8. The method of claim 1, further comprising the step of applying fourth electric fields along said first, second, third and fourth channels, wherein said sample band is transported from said region proximal to said second channel first end, across said junction toward said first channel first end, wherein portions of said sample band enter said third and fourth channels thereby causing said sample band to be further stretched and thinned while traversing the junction.

9. The method of claim 8, further comprising the step of reversing the direction of said fourth electric fields along said first and second channels at least once, wherein said sample band is transported across said junction multiple times causing said band to thin additionally with each traverse of said junction.

10. The method of claim 9, wherein the total number of reversal steps is odd, wherein, said sample band is finally positioned in said first end of said second channel proximate to said junction.

11. The method of claim 9, wherein the total number of reversal steps is even, wherein said sample band is finally positioned in said first end of said first channel proximate to said junction.

12. The method of claim 1, wherein said third and fourth channels are substantially co-linear along a secondary axis, wherein said secondary axis is perpendicular to said primary axis.

13. The method of claim 1, wherein each of said channels has a width.

14. The method of claim 13, wherein the widths of said channels are substantially the same.

15. The method of claim 14, wherein the junction formed at said intersection of said channels is square, and wherein each side of said junction is equal to said channel width.

16. The method of claim 13, wherein said junction has a height perpendicular to said common plane which is greater than the smallest channel width.

17. The method of claim 13, wherein a width of said junction along said primary axis is larger than the smallest channel width.

18. The method of claim 13, wherein the width of at least one channel is less than about 1000 microns.

19. The method of claim 1, wherein a portion of said microchannel system comprises a separation matrix disposed therein.

20. The method of claim 6, wherein said electric fields are controlled by the step of:

applying an electric potential to each of said electrodes, wherein each of said electric potentials comprise a magnitude and a polarity, and wherein each of said magnitudes and polarities is varied.

21. The method of claim 6, wherein said electric fields are controlled by varying a magnitude and a polarity of an electric current flowing to or from each of said electrodes.

22. A method for producing a thin sample band in a microchannel system, said method comprising the steps of:

a.) providing a junction formed at an intersection of at least four channels lying in a common plane, each of said channels having first and second ends, said first ends of said channels contiguous with said junction, wherein first and second channels are substantially co-linear along a primary axis, and wherein third and fourth channels lie on opposite sides of said primary axis;

b.) providing a reservoir and an electrode means at each of said second ends of said channels;

c.) providing a power supply connected to said electrodes, said power supply for applying electric fields along said channels;

d.) filling said channels, reservoirs and junction with a transport medium;

e.) introducing a quantity of a sample material into said reservoir at said second end of said third channel;

f.) applying first electric fields along said channels in order to induce transport of some of said sample material into said junction from said first, second and third channels, and out of said junction from the fourth channel, wherein a stream of said sample material is transported along said third channel in a direction toward said fourth channel, and wherein said stream is narrowed and focused at said junction under the influence of said electric fields wherein said narrowed sample stream continues to travel along said fourth channel away from said junction;

g.) removing said first electric fields;

h.) applying second electric fields along said third and fourth channels wherein said direction of travel of said narrowed sample stream is reversed, and wherein a portion of said narrowed stream is transported back into said third channel;

i.) removing said second electric fields; and j.) applying third electric fields along each of said channels in order to induce transport of some of said sample material into said junction from said first channel and out of said junction into said second, third, and fourth channels, wherein a portion of said narrowed sample stream enters said second channel forming a thinned sample band.

* * * * *